US008114635B2

(12) United States Patent
Klotz et al.

(10) Patent No.: US 8,114,635 B2
(45) Date of Patent: Feb. 14, 2012

(54) METHODS FOR OBTAINING MICROBIAL TRYPSIN MUTANTS HAVING CHYMOTRYPSIN ACTIVITY

(75) Inventors: Alan Klotz, Indianapolis, IN (US); Kimberly M. Brown, Elk Grove, CA (US); Elizabeth J. Zaretsky, Reno, NV (US)

(73) Assignee: Novozymes, Inc., Davis, CA (US)

( * ) Notice: Subject to any disclaimer, the term of this patent is extended or adjusted under 35 U.S.C. 154(b) by 0 days.

(21) Appl. No.: 12/708,433

(22) Filed: Feb. 18, 2010

(65) Prior Publication Data

US 2010/0151515 A1 Jun. 17, 2010

Related U.S. Application Data

(62) Division of application No. 12/022,771, filed on Jan. 30, 2008, now Pat. No. 7,705,137, which is a division of application No. 10/669,757, filed on Sep. 24, 2003, now Pat. No. 7,364,892.

(60) Provisional application No. 60/413,057, filed on Sep. 24, 2002.

(51) Int. Cl.
*C12P 21/00* (2006.01)

(52) U.S. Cl. .................................................... 435/71.1

(58) Field of Classification Search ........................ None
See application file for complete search history.

(56) References Cited

U.S. PATENT DOCUMENTS 5,693,520 A 12/1997 Branner et al.
6,060,305 A 5/2000 Royer et al.

FOREIGN PATENT DOCUMENTS

WO 9426925 A2 11/1994

OTHER PUBLICATIONS

Hedstrom et al, Methods Enzymol. 1991;202:671-87. Modulation of enzyme specificity by site-directed mutagenesis.*
Sidhu et al., 1993, Biochem. Cell. Biol. 71: 454-461.
Screen and St. Leger, 2000, Journal of Biological Chemistry 275: 6689-6694.
Hedstrom et al., 1992, Science 255: 1249-1253.
Yoshida, 1988, J Biochem 104, 451-456.
Witkowski, 1999, Biochemistry 38, 11643-11650.
Wisharti, 1995, J Biol Chem 270 (15), 26783-26785.
Wise, 1997, Electrophoresis 18, 1399-1409.
Rypniewski, 1993, Protein Engineering 6 (4), 341-348.
Kim, 1991, Biochem Biophys Res Com 181 (2), 707-713.
Henderson, 1987, J Bacteriol 169 (8), 377S-3784.
Hartley, 1964, Nature 201, 1284-1287.
Hames, In: Gel electrophoresis of proteins. Oxford University Press. pp. 30-32.
Guo, 2004, Proc Natl Acad Sci USA 101 (25), 920S-9210.
Geneseq, Accession No. AAA53331 from Yoder US patent 6060305 May 9, 2000.
Gencor Accession No. P00766 from Blow et al Nature 221 (5178), 337-340 (1969).
Gagne, 1993, Food Biotechnol 7 (3), 257-263.
Cosby, 2002, Promega Notes Magazine 61, 12-1.
Awad, 1972, J Biol Chem 247 (13), 4144-4154.

* cited by examiner

*Primary Examiner* — Sheridan Swope
(74) *Attorney, Agent, or Firm* — Robert L. Starnes

(57) ABSTRACT

The present invention relates to microbial trypsin variants having chymotrypsin-like activity, comprising: (a) a one or more substitutions corresponding to positions 144, 193, 198, 201, 218, 223, 227, 228, 229, 230, and 231 of amino acids 25 to 248 of SEQ ID NO: 2, (b) one or more deletions corresponding to positions 192, 197, and 226 of amino acids 25 to 248 of SEQ ID NO: 2; and (c) an insertion between positions corresponding to positions 224 and 225 of amino acids 25 to 248 of SEQ ID NO: 2. The present invention further relates to nucleotide sequences encoding microbial trypsin variants having chymotrypsin-like activity; nucleic acid constructs, expression vectors, and recombinant host cells comprising such nucleotide sequences; and methods of producing microbial trypsin variants having chymotrypsin-like activity or a precursor thereof.

14 Claims, 10 Drawing Sheets

```
ATC ATC AAC CAC TCT TCA CTC TTC AAC TCT CCT CTC TTG GAT ATC TAT CTC TTC ACC ATG      60
                                                                            Met
                                                                              1

GTC AAG TTC GCT TCC GTC GTT GCA CTT GTT GCT CCC CTG GCT GCT GCC GCT CCT CAG GAG     120
Val Lys Phe Ala Ser Val Val Ala Leu Val Ala Pro Leu Ala Ala Ala Ala Pro Gln Glu
                  5                  10                  15                  20

ATC CCC AAC ATT GTT GGT GGC ACT TCT GCC AGC GCT GGC GAC TTT CCC TTC ATC GTG AGC     180
Ile Pro Asn Ile Val Gly Gly Thr Ser Ala Ser Ala Gly Asp Phe Pro Phe Ile Val Ser
                 25                  30                  35                  40

ATT AGC CGC AAC GGT GGC CCC TGG TGT GGA GGT TCT CTC CTC AAC GCC AAC ACC GTC TTG     240
Ile Ser Arg Asn Gly Gly Pro Trp Cys Gly Gly Ser Leu Leu Asn Ala Asn Thr Val Leu
                 45                  50                  55                  60

ACT GCT GCC CAC TGC GTT TCC GGA TAC GCT CAG AGC GGT TTC CAG ATT CGT GCT GGC AGT     300
Thr Ala Ala His Cys Val Ser Gly Tyr Ala Gln Ser Gly Phe Gln Ile Arg Ala Gly Ser
                 65                  70                  75                  80

CTG TCT CGC ACT TCT GGT GGT ATT ACC TCC TCG CTT TCC TCC GTC AGA GTT CAC CCT AGC     360
Leu Ser Arg Thr Ser Gly Gly Ile Thr Ser Ser Leu Ser Ser Val Arg Val His Pro Ser
                 85                  90                  95                 100

TAC AGC GGA AAC AAC AAC GAT CTT GCT ATT CTG AAG CTC TCT ACT TCC ATC CCC TCC GGC     420
Tyr Ser Gly Asn Asn Asn Asp Leu Ala Ile Leu Lys Leu Ser Thr Ser Ile Pro Ser Gly
                105                 110                 115                 120

GGA AAC ATC GGC TAT GCT CGC CTG GCT GCT TCC GGC TCT GAC CCT GTC GCT GGA TCT TCT     480
Gly Asn Ile Gly Tyr Ala Arg Leu Ala Ala Ser Gly Ser Asp Pro Val Ala Gly Ser Ser
                125                 130                 135                 140
```

Fig. 1A

```
GCC ACT GTT GCT GGC TGG GGC GCT ACC TCT GAG GGC GGC AGC TCT ACT CCC GTC AAC CTT     540
Ala Thr Val Ala Gly Trp Gly Ala Thr Ser Glu Gly Gly Ser Ser Thr Pro Val Asn Leu
            145                 150                 155                 160

CTG AAG GTT ACT GTC CCT ATC GTC TCT CGT GCT ACC TGC CGA GCT CAG TAC GGC ACC TCC     600
Leu Lys Val Thr Val Pro Ile Val Ser Arg Ala Thr Cys Arg Ala Gln Tyr Gly Thr Ser
            165                 170                 175                 180

GCC ATC ACC AAC CAG ATG TTC TGT GCT GGT GTT TCT TCC GGT GGC AAG GAC TCT TGC CAG     660
Ala Ile Thr Asn Gln Met Phe Cys Ala Gly Val Ser Ser Gly Gly Lys Asp Ser Cys Gln
            185                 190                 195                 200

GGT GAC AGC GGC GGC CCC ATC GTC GAC AGC TCC AAC ACT CTT ATC GGT GCT GTC TCT TGG     720
Gly Asp Ser Gly Gly Pro Ile Val Asp Ser Ser Asn Thr Leu Ile Gly Ala Val Ser Trp
            205                 210                 215                 220

GGT AAC GGA TGT GCC CGA CCC AAC TAC TCT GGT GTC TAT GCC AGC GTT GGT GCT CTC CGC     780
Gly Asn Gly Cys Ala Arg Pro Asn Tyr Ser Gly Val Tyr Ala Ser Val Gly Ala Leu Arg
            225                 230                 235                 240

TCT TTC ATT GAC ACC TAT GCT TAA ATA CCT TGT TGG AAG CGT CGA GAT GTT CCT TGA ATA     840
Ser Phe Ile Asp Thr Tyr Ala
            245

TTC TCT AGC TTG AGT CTT GGA TAC GAA ACC TGT TTG AGA AAT AGG TTT CAA CGA GTT AAG     900

AAG ATA TGA GTT GAT TTC AGT TGG ATC TTA GTC CTG GTT GCT CGT AAT AGA GCA ATC TAG     960

ATA GCC CAA ATT GAA TAT GAA ATT TGA TGA AAA TAT TC                                   998
```

Fig. 1B

```
ATC ATC AAC CAC TCT TCA CTC TTC AAC TCT CCT CTC TTG GAT ATC TAT CTC TTC ACC ATG      60
                                                                            Met
                                                                              1

GTC AAG TTC GCT TCC GTC GTT GCA CTT GTT GCT CCC CTG GCT GCT GCC GCT CCT CAG GAG     120
Val Lys Phe Ala Ser Val Val Ala Leu Val Ala Pro Leu Ala Ala Ala Ala Pro Gln Glu
              5                  10                  15                  20

ATC CCC AAC ATT GTT GGT GGC ACT TCT GCC AGC GCT GGC GAC TTT CCC TTC ATC GTG AGC     180
Ile Pro Asn Ile Val Gly Gly Thr Ser Ala Ser Ala Gly Asp Phe Pro Phe Ile Val Ser
             25                  30                  35                  40

ATT AGC CGC AAC GGT GGC CCC TGG TGT GGA GGT TCT CTC CTC AAC GCC AAC ACC GTC TTG     240
Ile Ser Arg Asn Gly Gly Pro Trp Cys Gly Gly Ser Leu Leu Asn Ala Asn Thr Val Leu
             45                  50                  55                  60

ACT GCT GCC CAC TGC GTT TCC GGA TAC GCT CAG AGC GGT TTC CAG ATT CGT GCT GGC AGT     300
Thr Ala Ala His Cys Val Ser Gly Tyr Ala Gln Ser Gly Phe Gln Ile Arg Ala Gly Ser
             65                  70                  75                  80

CTG TCT CGC ACT TCT GGT GGT ATT ACC TCC TCG CTT TCC TCC GTC AGA GTT CAC CCT AGC     360
Leu Ser Arg Thr Ser Gly Gly Ile Thr Ser Ser Leu Ser Ser Val Arg Val His Pro Ser
             85                  90                  95                 100

TAC AGC GGA AAC AAC AAC GAT CTT GCT ATT CTG AAG CTC TCT ACT TCC ATC CCC TCC GGC     420
Tyr Ser Gly Asn Asn Asn Asp Leu Ala Ile Leu Lys Leu Ser Thr Ser Ile Pro Ser Gly
            105                 110                 115                 120

GGA AAC ATC GGC TAT GCT CGC CTG GCT GCT TCC GGC TCT GAC CCT GTC GCT GGA TCT TCT     480
Gly Asn Ile Gly Tyr Ala Arg Leu Ala Ala Ser Gly Ser Asp Pro Val Ala Gly Ser Ser
            125                 130                 135                 140
```

Fig. 2A

```
GCC ACT ACT GCT GGC TGG GGC GCT ACC TCT GAG GGC GGC AGC TCT ACT CCC GTC AAC CTT    540
Ala Thr Thr Ala Gly Trp Gly Ala Thr Ser Glu Gly Gly Ser Ser Thr Pro Val Asn Leu
            145                 150                 155                 160

CTG AAG GTT ACT GTC CCT ATC GTC TCT CGT GCT ACC TGC CGA GCT CAG TAC GGC ACC TCC    600
Leu Lys Val Thr Val Pro Ile Val Ser Arg Ala Thr Cys Arg Ala Gln Tyr Gly Thr Ser
            165                 170                 175                 180

GCC ATC ACC AAC CAG ATG TTC TGT GCT GGT GCT TCC GGT GGC TCT TCT TGC ATG GGT GAC    660
Ala Ile Thr Asn Gln Met Phe Cys Ala Gly Ala Ser Gly Gly Ser Ser Cys Met Gly Asp
            185                 190                 195                 200

AGC GGC GGC CCC ATC GTC GAC AGC TCC AAC ACT CTT ATC GGT ACT GTC TCT TGG GGT TCT    720
Ser Gly Gly Pro Ile Val Asp Ser Ser Asn Thr Leu Ile Gly Ile Val Ser Trp Gly Ser
            205                 210                 215                 220

GGA ACT TGT TCT ACT TCT ACT CCT GGT GTC TAT GCC AGC GTT GGT GCT CTC CGC TCT TTC    780
Gly Thr Cys Ser Thr Ser Thr Pro Gly Val Tyr Ala Ser Val Gly Ala Leu Arg Ser Phe
            225                 230                 235                 240

ATT GAC ACC TAT GCT TAA ATA CCT TGT TGG AAG CGT CGA GAT GTT CCT TGA ATA TTC TCT    840
Ile Asp Thr Tyr Ala
            245

AGC TTG AGT CTT GGA TAC GAA ACC TGT TTG AGA AAT AGG TTT CAA CGA GTT AAG AAG ATA    900

TGA GTT GAT TTC AGT TGG ATC TTA GTC CTG GTT GCT CGT AAT AGA GCA ATC TAG ATA GCC    960

CAA ATT GAA TAT GAA ATT TGA TGA AAA TAT TC                                         992
```

Fig. 2B

```
F. oxysporum trypsin                                        I V G G T S A S A G D F P F I V
F. oxysporum trypsin mutant                                 I V G G T S A S A G D F P F I V
Bovine chymotrypsin A                                       I V N G E E A V P G S W P W Q V

S I S R N G G P W C G G S L L N A N T V L T A A H C V S G Y A Q S G F Q I R A G
S I S R N G G P W C G G S L L N A N T V L T A A H C V S G Y A Q S G F Q I R A G
S L Q D K T G F H F C G G S L I N E W V V T A A H C - - - G V T T S D V V V A G

S L - - - S R T S G G I T S S L S S V R V H P S Y S - - G N N N D L A I L K L S
S L - - - S R T S G G I T S S L S S V R V H P S Y S - - G N N N D L A I L K L S
E F D Q G S S S E K I Q K L K I A K V F K N S K Y N S L T I N N D I T L L K L S

T S I P S G G N I G Y A R L A A S G S D P V A G S S A T V A G W G A T S E G G S
T S I P S G G N I G Y A R L A A S G S D P V A G S S A T T A G W G A T S E G G S
T A A S F S Q T V S A V C L P S A S D D F A A G T T C V T T G W G L T R Y T N A

S T P V N L L K V T V P I V S R A T C R A Q Y G T S A I T N Q M F C A G V S S G
S T P V N L L K V T V P I V S R A T C R A Q Y G T S A I T N Q M F C A G - A S G
N T P D R L Q Q A S L P L L S N T N C K K Y W G T - K I K D A M I C A G - - A S

G K D S C Q G D S G G P I V D S - - - S N T L I G A V S W G N G - C A R P N Y S
G - S S C M G D S G G P I V D S - - - S N T L I G I V S W G S G T C - S T S T P
G V S S C M G D S G G P L V C K K N G A W T L V G I V S W G S S T C - S T S T P

G V Y A S V G A L R S F I D T Y A
G V Y A S V G A L R S F I D T Y A
G V Y A R V T A L V N W V Q Q T L A A N
```

Fig. 3

SEQUENCE LISTING

```
<160> NUMBER OF SEQ ID NOS: 24

<210> SEQ ID NO 1
<211> LENGTH: 998
<212> TYPE: DNA
<213> ORGANISM: Fusarium oxysporum

<400> SEQUENCE: 1

atcatcaacc actcttcact cttcaactct cctctcttgg atatctatct cttcaccatg      60

gtcaagttcg cttccgtcgt tgcacttgtt gctcccctgg ctgctgccgc tcctcaggag     120

atccccaaca ttgttggtgg cacttctgcc agcgctggcg actttccctt catcgtgagc     180

attagccgca acggtggccc ctggtgtgga ggttctctcc tcaacgccaa caccgtcttg     240

actgctgccc actgcgtttc cggatacgct cagagcggtt tccagattcg tgctggcagt     300

ctgtctcgca cttctggtgg tattacctcc tcgctttcct ccgtcagagt tcaccctagc     360

tacagcggaa acaacaacga tcttgctatt ctgaagctct ctacttccat cccctccggc     420

ggaaacatcg gctatgctcg cctggctgct tccggctctg accctgtcgc tggatcttct     480

gccactgttg ctggctgggg cgctacctct gagggcggca gctctactcc cgtcaacctt     540

ctgaaggtta ctgtccctat cgtctctcgt gctacctgcc gagctcagta cggcacctcc     600

gccatcacca accagatgtt ctgtgctggt gtttcttccg gtggcaagga ctcttgccag     660

ggtgacagcg gcggccccat cgtcgacagc tccaacactc ttatcggtgc tgtctcttgg     720

ggtaacggat gtgcccgacc caactactct ggtgtctatg ccagcgttgg tgctctccgc     780

tctttcattg acacctatgc ttaaatacct tgttggaagc gtcgagatgt tccttgaata     840

ttctctagct tgagtcttgg atacgaaacc tgtttgagaa ataggtttca acgagttaag     900

aagatatgag ttgatttcag ttggatctta gtcctggttg ctcgtaatag agcaatctag     960

atagcccaaa ttgaatatga aatttgatga aaatattc                             998


<210> SEQ ID NO 2
<211> LENGTH: 248
<212> TYPE: PRT
<213> ORGANISM: Fusarium oxysporum

<400> SEQUENCE: 2
```

```
Met Val Lys Phe Ala Ser Val Val Ala Leu Val Ala Pro Leu Ala Ala
1               5                   10                  15

Ala Ala Pro Gln Glu Ile Pro Asn Ile Val Gly Gly Thr Ser Ala Ser
            20                  25                  30

Ala Gly Asp Phe Pro Phe Ile Val Ser Ile Ser Arg Asn Gly Gly Pro
        35                  40                  45

Trp Cys Gly Gly Ser Leu Leu Asn Ala Asn Thr Val Leu Thr Ala Ala
    50                  55                  60

His Cys Val Ser Gly Tyr Ala Gln Ser Gly Phe Gln Ile Arg Ala Gly
65                  70                  75                  80

Ser Leu Ser Arg Thr Ser Gly Gly Ile Thr Ser Ser Leu Ser Ser Val
                85                  90                  95

Arg Val His Pro Ser Tyr Ser Gly Asn Asn Asn Asp Leu Ala Ile Leu
            100                 105                 110

Lys Leu Ser Thr Ser Ile Pro Ser Gly Gly Asn Ile Gly Tyr Ala Arg
        115                 120                 125

Leu Ala Ala Ser Gly Ser Asp Pro Val Ala Gly Ser Ser Ala Thr Val
    130                 135                 140

Ala Gly Trp Gly Ala Thr Ser Glu Gly Gly Ser Ser Thr Pro Val Asn
145                 150                 155                 160

Leu Leu Lys Val Thr Val Pro Ile Val Ser Arg Ala Thr Cys Arg Ala
                165                 170                 175

Gln Tyr Gly Thr Ser Ala Ile Thr Asn Gln Met Phe Cys Ala Gly Val
            180                 185                 190

Ser Ser Gly Gly Lys Asp Ser Cys Gln Gly Asp Ser Gly Gly Pro Ile
        195                 200                 205

Val Asp Ser Ser Asn Thr Leu Ile Gly Ala Val Ser Trp Gly Asn Gly
    210                 215                 220

Cys Ala Arg Pro Asn Tyr Ser Gly Val Tyr Ala Ser Val Gly Ala Leu
225                 230                 235                 240

Arg Ser Phe Ile Asp Thr Tyr Ala
                245
```

<210> SEQ ID NO 3
<211> LENGTH: 992
<212> TYPE: DNA
<213> ORGANISM: Fusarium oxysporum

<400> SEQUENCE: 3

```
atcatcaacc actcttcact cttcaactct cctctcttgg atatctatct cttcaccatg      60

gtcaagttcg cttccgtcgt tgcacttgtt gctcccctgg ctgctgccgc tcctcaggag     120

atccccaaca ttgttggtgg cacttctgcc agcgctggcg actttccctt catcgtgagc     180

attagccgca acggtggccc ctggtgtgga ggttctctcc tcaacgccaa caccgtcttg     240

actgctgccc actgcgtttc cggatacgct cagagcggtt tccagattcg tgctggcagt     300

ctgtctcgca cttctggtgg tattacctcc tcgctttcct ccgtcagagt tcaccctagc     360

tacagcggaa acaacaacga tcttgctatt ctgaagctct ctacttccat cccctccggc     420

ggaaacatcg gctatgctcg cctggctgct tccggctctg accctgtcgc tggatcttct     480

gccactactg ctggctgggg cgctacctct gagggcggca gctctactcc cgtcaacctt     540

ctgaaggtta ctgtccctat cgtctctcgt gctacctgcc gagctcagta cggcacctcc     600

gccatcacca accagatgtt ctgtgctggt gcttccggtg gctcttcttg catgggtgac     660

agcggcggcc ccatcgtcga cagctccaac actcttatcg gtactgtctc ttggggttct     720
```

```
ggaacttgtt ctacttctac tcctggtgtc tatgccagcg ttggtgctct ccgctctttc    780

attgacacct atgcttaaat accttgttgg aagcgtcgag atgttccttg aatattctct    840

agcttgagtc ttggatacga aacctgtttg agaaataggt ttcaacgagt taagaagata    900

tgagttgatt tcagttggat cttagtcctg gttgctcgta atagagcaat ctagatagcc    960

caaattgaat atgaaatttg atgaaaatat tc                                  992


<210> SEQ ID NO 4
<211> LENGTH: 246
<212> TYPE: PRT
<213> ORGANISM: Fusarium oxysporum

<400> SEQUENCE: 4

Met Val Lys Phe Ala Ser Val Val Ala Leu Val Ala Pro Leu Ala Ala
1               5                   10                  15

Ala Ala Pro Gln Glu Ile Pro Asn Ile Val Gly Gly Thr Ser Ala Ser
            20                  25                  30

Ala Gly Asp Phe Pro Phe Ile Val Ser Ile Ser Arg Asn Gly Gly Pro
        35                  40                  45

Trp Cys Gly Gly Ser Leu Leu Asn Ala Asn Thr Val Leu Thr Ala Ala
    50                  55                  60

His Cys Val Ser Gly Tyr Ala Gln Ser Gly Phe Gln Ile Arg Ala Gly
65                  70                  75                  80

Ser Leu Ser Arg Thr Ser Gly Gly Ile Thr Ser Ser Leu Ser Ser Val
                85                  90                  95

Arg Val His Pro Ser Tyr Ser Gly Asn Asn Asn Asp Leu Ala Ile Leu
            100                 105                 110

Lys Leu Ser Thr Ser Ile Pro Ser Gly Gly Asn Ile Gly Tyr Ala Arg
        115                 120                 125

Leu Ala Ala Ser Gly Ser Asp Pro Val Ala Gly Ser Ser Ala Thr Thr
    130                 135                 140

Ala Gly Trp Gly Ala Thr Ser Glu Gly Gly Ser Ser Thr Pro Val Asn
145                 150                 155                 160

Leu Leu Lys Val Thr Val Pro Ile Val Ser Arg Ala Thr Cys Arg Ala
                165                 170                 175

Gln Tyr Gly Thr Ser Ala Ile Thr Asn Gln Met Phe Cys Ala Gly Ala
            180                 185                 190

Ser Gly Gly Ser Ser Cys Met Gly Asp Ser Gly Gly Pro Ile Val Asp
        195                 200                 205

Ser Ser Asn Thr Leu Ile Gly Ile Val Ser Trp Gly Ser Gly Thr Cys
    210                 215                 220

Ser Thr Ser Thr Pro Gly Val Tyr Ala Ser Val Gly Ala Leu Arg Ser
225                 230                 235                 240

Phe Ile Asp Thr Tyr Ala
                245


<210> SEQ ID NO 5
<211> LENGTH: 34
<212> TYPE: DNA
<213> ORGANISM: Fusarium oxysporum

<400> SEQUENCE: 5

ggatcttctg ccactactgc tggctggtaa gtcg                                 34


<210> SEQ ID NO 6
<211> LENGTH: 34
```

<212> TYPE: DNA
<213> ORGANISM: Fusarium oxysporum

<400> SEQUENCE: 6
cgacttacca gccagcagta gtggcagaag atcc 34

<210> SEQ ID NO 7
<211> LENGTH: 43
<212> TYPE: DNA
<213> ORGANISM: Fusarium oxysporum

<400> SEQUENCE: 7
gacacctatg cttaattaat accttgttgg aagcgtcgag atg 43

<210> SEQ ID NO 8
<211> LENGTH: 43
<212> TYPE: DNA
<213> ORGANISM: Fusarium oxysporum

<400> SEQUENCE: 8
catctcgacg cttccaacaa ggtattaatt aagcataggt gtc 43

<210> SEQ ID NO 9
<211> LENGTH: 74
<212> TYPE: DNA
<213> ORGANISM: Fusarium oxysporum

<400> SEQUENCE: 9
agtacggcac ctccgccatc accaaccaga tgttctgtgc tggtgcttcc ggtggctctt 60
cttgcatggg tgac 74

<210> SEQ ID NO 10
<211> LENGTH: 74
<212> TYPE: DNA
<213> ORGANISM: Fusarium oxysporum

<400> SEQUENCE: 10
agcggcggcc ccatcgtcga cagctccaac actcttatcg gtatcgtctc ttggggttct 60
ggaacttgtt ctac 74

<210> SEQ ID NO 11
<211> LENGTH: 64
<212> TYPE: DNA
<213> ORGANISM: Fusarium oxysporum

<400> SEQUENCE: 11
ttctactcct ggtgtctatg ccagcgttgg tgctctccgc tctttcattg acacctatgc 60
ttaa 64

<210> SEQ ID NO 12
<211> LENGTH: 81
<212> TYPE: DNA
<213> ORGANISM: Fusarium oxysporum

<400> SEQUENCE: 12
ttaagcatag gtgtcaatga aagagcggag agcaccaacg ctggcataga caccaggagt 60
agaagtagaa caagttccag a 81

<210> SEQ ID NO 13
<211> LENGTH: 74
<212> TYPE: DNA
<213> ORGANISM: Fusarium oxysporum

<400> SEQUENCE: 13
accccaagag acgataccga taagagtgtt ggagctgtcg acgatggggc cgccgctgtc 60
acccatgcaa gaag 74

<210> SEQ ID NO 14
<211> LENGTH: 56
<212> TYPE: DNA
<213> ORGANISM: Fusarium oxysporum

<400> SEQUENCE: 14
agccaccgga agcaccagca cagaacatct ggttggtgat ggcggaggtg ccgtat 56

<210> SEQ ID NO 15
<211> LENGTH: 24
<212> TYPE: DNA
<213> ORGANISM: Fusarium oxysporum

<400> SEQUENCE: 15
cccgagctca gtacggcacc tccg 24

<210> SEQ ID NO 16
<211> LENGTH: 22
<212> TYPE: DNA
<213> ORGANISM: Fusarium oxysporum

<400> SEQUENCE: 16
cccttaatta agcataggtg tc 22

<210> SEQ ID NO 17
<211> LENGTH: 21
<212> TYPE: DNA
<213> ORGANISM: Fusarium oxysporum

<400> SEQUENCE: 17
ttcatattca atttgggcta t 21

<210> SEQ ID NO 18
<211> LENGTH: 21
<212> TYPE: DNA
<213> ORGANISM: Fusarium oxysporum

<400> SEQUENCE: 18
tatctcagat gtcagagaac g 21

<210> SEQ ID NO 19
<211> LENGTH: 21
<212> TYPE: DNA
<213> ORGANISM: Fusarium oxysporum

<400> SEQUENCE: 19
atggtcaagt tcgcttccgt c 21

<210> SEQ ID NO 20
<211> LENGTH: 21
<212> TYPE: DNA
<213> ORGANISM: Fusarium oxysporum

<400> SEQUENCE: 20
gctctgaccc tgtcgctgga t 21

<210> SEQ ID NO 21
<211> LENGTH: 21

-continued

```
<212> TYPE: DNA
<213> ORGANISM: Fusarium oxysporum

<400> SEQUENCE: 21

ctgccaacat agataatgag g                                              21


<210> SEQ ID NO 22
<211> LENGTH: 21
<212> TYPE: DNA
<213> ORGANISM: Fusarium oxysporum

<400> SEQUENCE: 22

gttggatctt agtcctggtt g                                              21


<210> SEQ ID NO 23
<211> LENGTH: 21
<212> TYPE: DNA
<213> ORGANISM: Fusarium oxysporum

<400> SEQUENCE: 23

atccaagact caagctagag a                                              21


<210> SEQ ID NO 24
<211> LENGTH: 229
<212> TYPE: PRT
<213> ORGANISM: Bovine chymotrypsin

<400> SEQUENCE: 24

Ile Val Asn Gly Glu Glu Ala Val Pro Gly Ser Trp Pro Trp Gln Val
1               5                   10                  15

Ser Leu Gln Asp Lys Thr Gly Phe His Phe Cys Gly Gly Ser Leu Ile
            20                  25                  30

Asn Glu Trp Val Val Thr Ala Ala His Cys Gly Val Thr Thr Ser Asp
        35                  40                  45

Val Val Val Ala Gly Glu Phe Asp Gln Gly Ser Ser Ser Glu Lys Ile
    50                  55                  60

Gln Lys Leu Lys Ile Ala Lys Val Phe Lys Asn Ser Lys Tyr Asn Ser
65                  70                  75                  80

Leu Thr Ile Asn Asn Asp Ile Thr Leu Leu Lys Leu Ser Thr Ala Ala
                85                  90                  95

Ser Phe Ser Gln Thr Val Ser Ala Val Cys Leu Pro Ser Ala Ser Asp
            100                 105                 110

Asp Phe Ala Ala Gly Thr Thr Cys Val Thr Thr Gly Trp Gly Leu Thr
        115                 120                 125

Arg Tyr Thr Asn Ala Asn Thr Pro Asp Arg Leu Gln Gln Ala Ser Leu
    130                 135                 140

Pro Leu Leu Ser Asn Thr Asn Cys Lys Lys Tyr Trp Gly Thr Lys Ile
145                 150                 155                 160

Lys Asp Ala Met Ile Cys Ala Gly Ala Ser Gly Val Ser Ser Cys Met
                165                 170                 175

Gly Asp Ser Gly Gly Pro Leu Val Cys Lys Lys Asn Gly Ala Trp Thr
            180                 185                 190

Leu Val Gly Ile Val Ser Trp Gly Ser Ser Thr Cys Ser Thr Ser Thr
        195                 200                 205

Pro Gly Val Tyr Ala Arg Val Thr Ala Leu Val Asn Trp Val Gln Gln
    210                 215                 220

Thr Leu Ala Ala Asn
225
```

METHODS FOR OBTAINING MICROBIAL TRYPSIN MUTANTS HAVING CHYMOTRYPSIN ACTIVITY

CROSS-REFERENCE TO RELATED APPLICATION

This application is a divisional of U.S. application Ser. No. 12/022,771, filed Jan. 30, 2008, now U.S. Pat. No. 7,705,137, which is a divisional of U.S. application Ser. No. 10/669,757, filed Sep. 24, 2003, now U.S. Pat. No. 7,364,892, which claims priority from U.S. Provisional Application Ser. No. 60/413,057, filed on Sep. 24, 2002, which applications are fully incorporated herein by reference.

BACKGROUND OF THE INVENTION

1. Field of the Invention

The present invention relates to variants having chymotrypsin-like activity, nucleic acids encoding the variants, methods of producing the variants, and methods for using the variants.

2. Description of the Related Art

Proteolytic enzymes have widespread commercial application and have been successfully implemented in different industries such as the detergent, leather, chemical, agricultural, pharmaceutical, food, and dairy industries. Chymotrypsin and trypsin are two such proteolytic enzymes available from mammalian sources. Chymotrypsin preferentially cleaves at the C-terminal side of peptide bonds of the L-isomers of tyrosine, phenylalanine, and tryptophan. Trypsin preferentially cleaves at the C-terminal side of peptide bonds of the L-isomers of lysine and arginine. Mammalian trypsin and chymotrypsin are synthesized as precursors known as trypsinogen and chymotrypsinogen, respectively, having both an amino-terminal signal peptide to direct secretion as well as a propeptide that silences enzyme activity until it is proteolytically removed with concomitant activation of the enzyme. Cleavage of the propeptide requires a highly specific serine endoprotease activity.

Four chymotrypsin-like serine proteases have been identified from *Streptomyces griseus*, namely SGT, SGPA, SGPB, and SGPE (Awad et al., 1972, *Journal of Biological Chemistry* 247: 4144-4154; Yoshida et al., 1988, *J. Biochem.* (Tokyo) 104: 451-456). The gene sequences of these chymotrypsin-like serine proteases have also been disclosed (Henderson et al., 1987, *Journal of Bacteriology* 169: 3778-3784; Sidhu et al., 1993, *Biochem. Cell. Biol.* 71: 454-461; and Kim et al., 1991, *Biochem. Biophys. Res. Commun.* 181: 707-713). Sachdev et al., 1994, *Journal of Biological Chemistry* 269: 20167-20171, disclose a *Streptomyces griseus* chymotrypsin-like serine protease designated SCPC and the gene encoding the protease. Screen and St. Leger, 2000, *Journal of Biological Chemistry* 275: 6689-6694, disclose a chymotrypsin-like enzyme from the deuteromycete *Metarhizium anisopliae.*

Hedstrom et al., 1992, *Science* 255: 1249-1253 disclose the protein engineering of a mammalian trypsin gene to code for a polypeptide with a functional chymotrypsin substrate profile by site-directed mutagenesis of the S1 binding site and surface loops of the binding pocket of trypsin with analogous residues of chymotrypsin.

While chymotrypsin is obtainable from mammalian sources and chymotrypsin-like enzymes are available from a few microbial sources, there is a need in the art for new sources of chymotrypsin-like enzymes to provide alternative sources to establish new enzymatic processes and to provide improved cost and performance.

The object of the present invention is to provide protein engineered microbial polypeptides having chymotrypsin-like activity from microbial trypsin-like enzymes.

SUMMARY OF THE INVENTION

The present invention relates to microbial trypsin variants having chymotrypsin-like activity, comprising one or more modifications selected from the group consisting of:

(a) a substitution at one or more positions corresponding to positions 144, 193, 198, 201, 218, 223, 227, 228, 229, 230, and 231 of amino acids 25 to 248 of SEQ ID NO: 2, (b) a deletion at one or more positions corresponding to positions 192, 197, and 226 of amino acids 25 to 248 of SEQ ID NO: 2; and (c) an insertion between positions corresponding to positions 224 and 225 of amino acids 25 to 248 of SEQ ID NO: 2;

wherein the microbial trypsin is (a) a polypeptide having an amino acid sequence which has at least 70% identity to amino acids 25 to 248 of SEQ ID NO: 2; or (b) a polypeptide encoded by a nucleotide sequence which hybridizes under at least low stringency conditions with nucleotides 202 to 801 of SEQ ID NO: 1 or its complementary strand, wherein the variant has chymotrypsin-like activity and has an amino acid sequence that has at least 70% identity to the amino acid sequence of the microbial trypsin.

A method for obtaining a variant of a microbial trypsin, comprising:

(a) introducing one or more modifications selected from the group consisting of:

(1) a substitution at one or more positions corresponding to positions 144, 193, 198, 201, 218, 223, 227, 228, 229, 230, and 231 of amino acids 25 to 248 of SEQ ID NO: 2, (2) a deletion at one or more positions corresponding to positions 192, 197, and 226 of amino acids 25 to 248 of SEQ ID NO: 2; and (3) an insertion between positions corresponding to positions 224 and 225 of amino acids 25 to 248 of SEQ ID NO: 2;

wherein the microbial trypsin is (a) a polypeptide having an amino acid sequence which has at least 70% identity to amino acids 25 to 248 of SEQ ID NO: 2; or (b) a polypeptide encoded by a nucleotide sequence which hybridizes under at least low stringency conditions with nucleotides 202 to 801 of SEQ ID NO: 1 or its complementary strand, wherein the variant has chymotrypsin-like activity and has an amino acid sequence that has at least 70% identity to the amino acid sequence of the microbial trypsin; and (b) recovering the variant having chymotrypsin-like activity.

The present invention further relates to nucleotide sequences encoding microbial trypsin variants having chymotrypsin-like activity; nucleic acid constructs, expression vectors, and recombinant host cells comprising such nucleotide sequences; and methods of producing microbial trypsin variants having chymotrypsin-like activity or a precursor thereof.

The present invention further relates to using a microbial trypsin variant having chymotrypsin-like activity in detergents.

BRIEF DESCRIPTION OF THE FIGURES

FIG. 1 shows the DNA sequence and deduced amino acid sequence of a *Fusarium oxysporum* trypsinogen-like protein (SEQ ID NO: 1 and SEQ ID NO: 2, respectively).

FIG. 2 shows the DNA sequence and deduced amino acid sequence of a *Fusarium oxysporum* trypsinogen-like protein engineered to encode a polypeptide having chymotrypsin-like activity (SEQ ID NO: 3 and SEQ ID NO: 4, respectively).

FIG. 3 shows a comparative alignment of the amino acid sequences of a *Fusarium oxysporum* trypsin (SEQ ID NO: 2), a *Fusarium oxysporum* trypsin variant having chymotrypsin activity (SEQ ID NO: 4), and bovine chymotrypsin A (SEQ ID NO: 24).

DETAILED DESCRIPTION OF THE INVENTION

Figure 4:
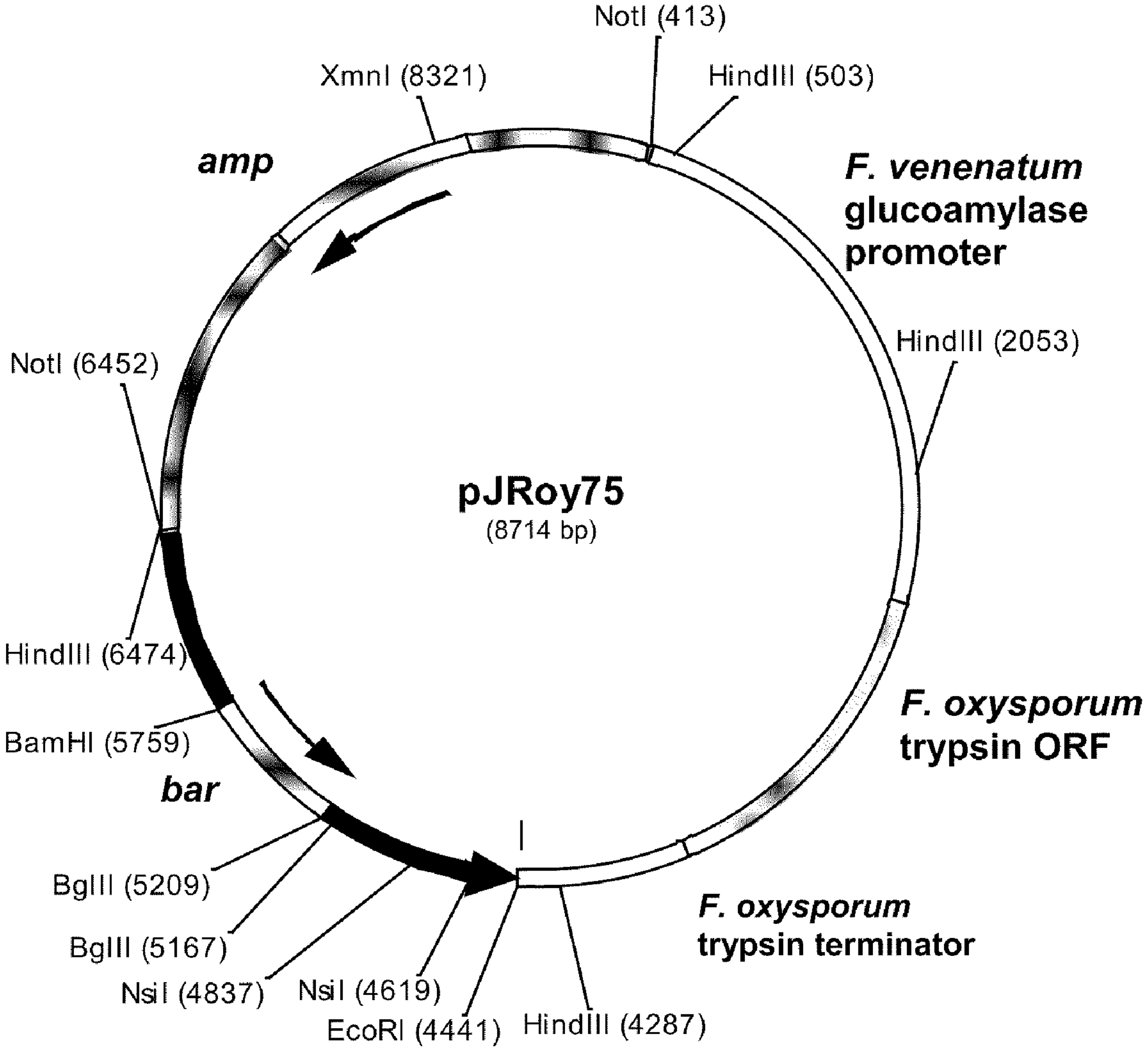
FIG. 4 shows a restriction map of pJRoy75.

The present invention relates to microbial trypsin variants having chymotrypsin-like activity, comprising one or more modifications selected from the group consisting of: (a) a substitution at one or more positions corresponding to positions 144, 193, 198, 201, 218, 223, 227, 228, 229, 230, and 231 of amino acids 25 to 248 of SEQ ID NO: 2, (b) a deletion at one or more positions corresponding to positions 192, 197, and 226 of amino acids 25 to 248 of SEQ ID NO: 2; and (c) an insertion between positions corresponding to positions 224 and 225 of amino acids 25 to 248 of SEQ ID NO: 2; wherein the microbial trypsin is (a) a polypeptide having an amino acid sequence which has at least about 70%, preferably at least about 75%, more preferably at least about 80%, more preferably at least about 85%, even more preferably at least about 90%, most preferably at least about 95%, and even most preferably at least about 97% identity to amino acids 25 to 248 of SEQ ID NO: 2; or (b) a polypeptide encoded by a nucleotide sequence which hybridizes under low stringency conditions, preferably medium stringency conditions, more preferably medium-high stringency conditions, even more preferably high stringency conditions, and most preferably very high stringency conditions with nucleotides 202 to 801 of SEQ ID NO: 1 or its complementary strand, wherein the variant has chymotrypsin-like activity and has an amino acid sequence that has at least 70%, preferably at least about 75%, more preferably at least about 80%, more preferably at least about 85%, even more preferably at least about 90%, most preferably at least about 95%, and even most preferably at least about 97% identity to the amino acid sequence of the microbial trypsin.

DEFINITIONS

The term “variant” is defined herein as a microbial trypsin mutant having chymotrypsin-like activity, wherein the variant comprises one or more modifications or alterations, such as substitution(s), insertion(s), deletion(s), and/or truncation(s) of one or more specific amino acid residue(s) at one or more specific position(s) in the microbial trypsin.

The term “trypsin” is defined herein as an endopeptidase which catalyzes the hydrolysis of carboxylic acid amides with preferential cleavage at the C-terminal side of Arg or Lys (E.C. 3.4.21.4). For purposes of the present invention, trypsin activity is determined using N-benzoyl-L-arginine p-nitroanilide hydrochloride as substrate according to the procedure Gaertner and Puigserver, 1992, *Enzyme Microb. Technol.* 14: 150, at 25° C. with 2 mg of N-benzoyl-L-arginine p-nitroanilide hydrochloride per ml of 100 mM MOPS buffer, 4 mM $CaCl_2$, 0.01% Triton X-100, pH 7.5. The assay is monitored at 405 nm. One unit of trypsin activity is defined as 1.0 μmole of N-benzoyl-L-arginine p-nitroanilide hydrolyzed per minute at 25° C., pH 7.5.

The term “parent trypsin” describes a trypsin isolated from a natural microbial source, wherein subsequent substitution, deletion, and/or insertion of one or more amino acids are made to protein engineer the enzyme to one with chymotrypsin-like activity. Alternatively the term “parent trypsin” may be termed “wild type trypsin.” The parent may be a naturally occurring (wild type) polypeptide, or it may even be a variant thereof, prepared by any suitable means. For instance, the parent protein may be a variant of a naturally occurring polypeptide which has been modified or altered in the amino acid sequence. A parent may also be an allelic variant which is any of two or more alternative forms of a gene occupying the same chromosomal locus. An allelic variant of a polypeptide is a polypeptide encoded by the corresponding allelic variant of a gene.

The term “wild-type” microbial trypsin denotes a microbial trypsin expressed by a naturally occurring microorganism, such as a bacterium, yeast, or filamentous fungus found in nature.

The term “chymotrypsin” is defined herein as an endopeptidase which catalyzes the hydrolysis of carboxylic acid amides with preferential cleavage at the C-terminal side of Tyr, Trp, Phe, or Leu (E.C. 3.4.21.1). For purposes of the present invention, chymotrypsin activity is determined using N-succinyl-Ala-Ala-Pro-Phe p-nitroanilide as substrate at 25° C. with 2 mg of N-benzoyl-L-arginine p-nitroanilide hydrochloride per ml of 100 mM MOPS buffer, 4 mM $CaCl_2$, 0.01% Triton X-100, pH 7.5. The assay is monitored at 405 nm. One unit of chymotrypsin activity is defined as 1.0 μmole of N-succinyl-Ala-Ala-Pro-Phe p-nitroanilide hydrolyzed per minute at 25° C., pH 7.5.

The term “trypsin-like” is defined herein as an enzyme having an activity similar to that of trypsin, i.e., cleaving peptide bonds at the C-terminal side of Arg or Lys, obtained from a microbial source. The terms “trypsin-like enzyme” and “microbial trypsin” are used interchangeably herein.

The term “chymotrypsin-like” is defined herein as an enzyme having an activity similar to that of chymotrypsin, i.e., cleaving peptide bonds at the C-terminal side of Tyr, Trp, Phe, or Leu.

In the present invention, the terms “trypsin”, “chymotrypsin”, “trypsin-like”, and “chymotrypsin-like” will be understood to encompass only the mature active enzymes. Such enzymes are biosynthesized as precursors having both an amino-terminal signal peptide to direct secretion as well as a propeptide that silences enzyme activity until it is proteolytically removed with concomitant activation of the enzyme. The term “precursor” is defined herein as the prepro form or pro form of trypsin, chymotrypsin, trypsin-like protease, and chymotrypsin-like protease.

The phrase “positions corresponding to positions” of amino acids 25 to 248 of SEQ ID NO: 2, or various wording thereof, is defined herein as analogous positions of the microbial trypsin that correspond to amino acids 25 to 248 of SEQ ID NO: 2.

Conventions for Designation of Variants

In the present invention, a specific numbering of amino acid residue positions in the variants is employed. For example, by aligning the amino acid sequences of known microbial trypsins, it is possible to designate an amino acid position number to any amino acid residue in any microbial trypsin. The same applies to chymotrypsin and chymotrypsin-like enzymes.

Using the numbering system originating from the amino acid sequence of the microbial trypsin disclosed in SEQ ID NO: 2, aligned with the amino acid sequence of a number of other microbial trypsins, it is possible to indicate the position of an amino acid residue in a microbial trypsin in regions of structural homology.

Multiple alignments of protein sequences may be made using "ClustalW" (Thompson, J. D., Higgins, D. G. and Gibson, T. J., 1994, CLUSTAL W: Improving the sensitivity of progressive multiple sequence alignment through sequence weighting, positions-specific gap penalties and weight matrix choice, *Nucleic Acids Research* 22: 4673-4680). Multiple alignments of DNA sequences may be done using the protein alignment as a template, replacing the amino acids with the corresponding codon from the DNA sequence.

Pairwise sequence comparison algorithms in common use are adequate to detect similarities between protein sequences that have not diverged beyond the point of approximately 20-30% sequence identity (Doolittle, 1992, *Protein Sci.* 1: 191-200; Brenner et al., 1998, *Proc. Natl. Acad. Sci. USA* 95, 6073-6078). However, truly homologous proteins with the same fold and similar biological function have often diverged to the point where traditional sequence-based comparison fails to detect their relationship (Lindahl and Elofsson, 2000, *J. Mol. Biol.* 295: 613-615). Greater sensitivity in sequence-based searching can be attained using search programs that utilize probabilistic representations of protein families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the protein of interest has one or more representatives in the protein structure databases. Programs such as GenTHREADER (Jones 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al (2000, *J. Mol. Biol.* 313: 903-919) can be used to align a sequence of unknown structure with the superfamily models present in the SCOP database. These alignments can in turn be used to generate homology models for the protein of interest, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. These alignments can be used to predict the structurally and functionally corresponding amino acid residues in proteins within the same structural superfamily. This information, along with information derived from homology modeling and profile searches, can be used to predict which residues to mutate when moving mutations of interest from one protein to a close or remote homolog.

In describing the various microbial trypsin variants having chymotrypsin-like activity, the nomenclature described below is adapted for ease of reference. In all cases, the accepted IUPAC single letter or triple letter amino acid abbreviations are employed. The following nomenclature is employed for amino acids: A=Ala=Alanine; V=Val=Valine; L=Leu=Leucine; I=Ile=Isoleucine; P=Pro=Proline; F=Phe=Phenylalanine; W=Trp=Tryptophan; M=Met=Methionine; G=Gly=Glycine; S=Ser=Serine; T=Thr=Threonine; C=Cys=Cysteine; Y=Tyr=Tyrosine; N=Asn=Asparagine; Q=Gln=Glutamine; D=Asp=Aspartic Acid; E=Glu=Glutamic Acid; K=Lys=Lysine; R=Arg=Arginine; H=His=Histidine; and X=Xaa=any amino acid.

Substitutions. For an amino acid substitution, the following nomenclature is used: [Original amino acid; Position; Substituted amino acid]. Accordingly, the substitution of threonine with alanine at position 226 is designated as "Thr226Ala" or "T226A". Multiple mutations are separated by addition marks ("+"), e.g., "Gly205Arg+Ser411Phe" or "G205R+S411F", representing mutations at positions 205 and 411 substituting glycine (G) with arginine (R), and serine (S) with phenylalanine (F), respectively.

Deletions. For an amino acid deletion, the following nomenclature is used: [Original amino acid; Position*]. Accordingly, the deletion of glycine at position 195 is designated as "Gly195*" or "G195*". Multiple deletions are separated by addition marks ("+"), e.g., "Gly195*+Ser411*" or "G195*+S411*".

Insertions. For an amino acid insertion, the following nomenclature is used: [Original amino acid; Position; original amino acid; new inserted amino acid]. Accordingly the insertion of lysine after glycine at position 195 is designated "Gly195GlyLys" or "G195GK". Multiple insertions of amino acids are designated [Original amino acid; Position*; original amino acid; new inserted amino acid #1; new inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example the sequences would be:

| Parent: | Variant: |
|---|---|
| 195<br>G | 195 195a 195b<br>G - K - A |

Degenerate indications. For degenerate indications where an amino acid residue identical to the existing amino acid residue is inserted, degeneracy in the nomenclature arises. For example, a glycine inserted after the glycine in the above example would be indicated by "G195GG". Given that an alanine is present in position 194, the same actual change could just as well be indicated as "A194AG":

| | Parent: | Variant: |
|---|---|---|
| Numbering I: | 194 195 | 194 195 195a |
| Sequence: | A - G | A - G - G |
| Numbering II: | | 194 194a 195 |

Such instances will be apparent to the skilled person, and the indication "G195GG" and corresponding indications for this type of insertion is thus meant to comprise such equivalent degenerate indications.

If amino acid sequence segments are repeated in the parent polypeptide and/or in the variant, it will be apparent to the skilled person that equivalent degenerate indications arise, also when alterations other than insertions are listed such as deletions and/or substitutions. For instance, the deletion of two consecutive amino acids "AG" in the sequence "AGAG" from position 194-97, may be written as "A194*+G195*" or "A196*+G197*":

| | Parent: | Variant: |
|---|---|---|
| Numbering I: | 194 195 196 197 | 194 195 |
| Sequence: | A - G - A - G | A - G |
| Numbering II: | | 196 197 |

Multiple modifications. Variants comprising multiple modifications are separated by addition marks ("+"), e.g., "Arg170Tyr+Gly195Glu" or "R170Y+G195E" representing modifications in positions 170 and 195 substituting tyrosine and glutamic acid for arginine and glycine, respectively. Thus, "Tyr167Gly,Ala,Ser,Thr+Arg170Gly,Ala,Ser,Thr" designates the following variants:

"Tyr167Gly+Arg 170Gly", "Tyr167Gly+Arg170Ala", "Tyr167Gly+Arg 170Ser",

"Tyr167Gly+Arg170Thr", "Tyr167Ala+Arg170Gly", "Tyr167Ala+Arg170Ala",

"Tyr167Ala+Arg170Ser", "Tyr167Ala+Arg 170Thr", "Tyr167Ser+Arg 170Gly",

"Tyr167Ser+Arg170Ala", "Tyr167Ser+Arg170Ser", "Tyr167Ser+Arg170Thr",

"Tyr167Thr+Arg 170Gly", "Tyr167Thr+Arg170Ala", "Tyr167Thr+Arg170Ser", and

"Tyr167Thr+Arg170Thr".

This nomenclature is particularly relevant to modifications involving substituting, inserting or deleting amino acid residues having specific common properties. Such modifications are referred to as conservative amino acid modification(s). Examples of conservative modifications are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid modifications, which do not generally alter the specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as the reverse. (See, http://www.compbio.dundee.ac.uk/papers/amas/amas3d.html; Taylor, 1986, *J. Theor. Biol.* 119, 205-218).

Microbial Trypsin-Like Enzymes or Trypsinogen-Like Proteins

In the present invention, a microbial trypsin or trypsinogen, and the nucleotide sequences thereof, may be obtained from microorganisms of any genus. For purposes of the present invention, the term "obtained from" as used herein in connection with a given source shall mean that the microbial trypsin or trypsinogen encoded by a nucleotide sequence is produced by the source or by a cell in which the nucleotide sequence from the source has been inserted.

In a preferred embodiment, the microbial trypsin is the trypsin-like enzyme produced by *Fusarium oxysporum* as described in U.S. Pat. Nos. 5,843,753 and 5,807,729, i.e., the microbial trypsin of amino acids 25 to 248 of SEQ ID NO: 2, which is encoded by nucleotides 202 to 801 of SEQ ID NO: 1. The sequence of SEQ ID NO: 1 is obtainable from *Fusarium oxysporum* DSM 2672 (U.S. Pat. No. 5,693,520). In another preferred embodiment, the microbial trypsinogen is the trypsinogen-like protein encoded by *Fusarium oxysporum* as described in U.S. Pat. Nos. 5,843,753 and 5,807,729, i.e., the microbial trypsinogen of SEQ ID NO: 2, which is encoded by nucleotides 131 to 801 of SEQ ID NO: 1. In another preferred embodiment, the microbial trypsin is the trypsin-like enzyme and precursor thereof produced by strains of *Amycolata* and *Amycolatopsis* as described in U.S. Pat. No. 5,948,746.

The nucleotide sequence of SEQ ID NO: 1 or a subsequence thereof, as well as the amino acid sequence of SEQ ID NO: 2 or a fragment thereof, may be used to design a nucleic acid probe to identify and clone DNA encoding trypsin-like enzymes from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labelled, for example, with $^{32}P$, $^{3}H$, $^{35}S$, biotin, or avidin, for detecting the corresponding gene.

In a preferred embodiment, the nucleic acid probe is a nucleotide sequence which encodes the trypsinogen-like protein of SEQ ID NO: 2, or a subsequence thereof. In another preferred embodiment, the nucleic acid probe is SEQ ID NO: 1. In another preferred embodiment, the nucleic acid probe is the mature polypeptide coding region of SEQ ID NO: 1, i.e., nucleotides 202 to 801. In another preferred embodiment, the nucleic acid probe is the nucleotide sequence contained in *Fusarium oxysporum* DSM 2672, wherein the nucleotide sequence encodes a trypsin-like enzyme or a precursor thereof.

Thus, a genomic DNA or cDNA library prepared from such other microorganisms of different genera or species may be screened for DNA which hybridizes with the probes described above and which encode trypsin-like enzymes or precursors thereof. Genomic or other DNA from such strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 1 or a subsequence thereof, the carrier material is used in a Southern blot. For purposes of the present invention, hybridization indicates that the nucleotide sequence hybridizes to a labeled nucleic acid probe corresponding, for example, to the nucleotide sequence shown in SEQ ID NO: 1, its complementary strand, or a subsequence thereof, under low to very high stringency conditions. Molecules to which the nucleic acid probe hybridizes under these conditions are detected using X-ray film.

For long probes of at least 100 nucleotides in length, low to very high stringency conditions are defined as prehybridization and hybridization at 42° C. in 5×SSPE, 0.3% SDS, 200 µg/ml sheared and denatured salmon sperm DNA, and either 25% formamide for low stringencies, 35% formamide for medium and medium-high stringencies, or 50% formamide for high and very high stringencies, following standard Southern blotting procedures. The carrier material is then washed three times each for 15 minutes using 2×SSC, 0.2% SDS preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures. The carrier material is then washed once in 6×SCC plus 0.1% SDS for 15 minutes and twice each for 15 minutes using 6×SSC at 5° C. to 10° C. below the calculated $T_m$.

As noted above, the microbial trypsin (or a precursor thereof) and the nucleotide sequence thereof may be obtained from strains of different genera or species. The microbial trypsin (or a precursor thereof) and the nucleotide sequence thereof may be obtained from a bacterium such as a *Bacillus* strain, e.g., *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis*; or a *Streptomyces* strain, e.g., a *Streptomyces lividans* or *Streptomyces murinus*; or a gram negative bacterial strain, e.g., an *E. coli* or a *Pseudomonas* sp. The microbial trypsin (or a precursor thereof) and the nucleotide sequence thereof may also be obtained from actinomycete strains, e.g., *Amycolata* and *Amycolatopsis* strains (see, U.S. Pat. No. 5,948,746).

The microbial trypsin (or a precursor thereof) and the nucleotide sequence thereof may also be obtained from a fungal strain, and more preferably a yeast strain such as a *Candida, Chaetomium, Kluyveromyces, Pichia, Saccharomyces, Schizosaccharomyces*, or *Yarrowia* strain; or more preferably a filamentous fungal strain such as an *Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium*, or *Trichoderma* strain.

In a preferred embodiment, the microbial trypsin (or a precursor thereof) and the nucleotide sequence thereof may be obtained from *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis.*

In another preferred embodiment, the microbial trypsin (or a precursor thereof) and the nucleotide sequence thereof may be obtained from *Aspergillus aculeatus, Aspergillus awamori, Aspergillus foetidus, Aspergillus fumigatus, Aspergillus japonicus, Aspergillus nidulans, Aspergillus niger, Aspergillus oryzae, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Trichoderma harzianum, Trichoderma koningii, Trichoderma longibrachiatum, Trichoderma reesei*, or *Trichoderma viride.*

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL). Furthermore, the microbial trypsin (or a precursor thereof) may be identified and obtained from other sources including microorganisms isolated from nature (e.g., soil, composts, water, etc.) using the above-mentioned probes and methods.

Techniques for isolating microorganisms from natural habitats are well known in the art. A nucleotide sequence encoding a trypsin-like enzyme may then be obtained by similarly screening a genomic or cDNA library of another microorganism. Once a nucleotide sequence has been detected with the probe(s) described herein, the sequence may be cloned and sequenced by utilizing techniques which are known in the art (see, e.g., J. Sambrook, E. F. Fritsch, and T. Maniatus, 1989, *Molecular Cloning, A Laboratory Manual,* 2d edition, Cold Spring Harbor, N.Y.).

As defined herein, an "isolated microbial trypsin" is a polypeptide which is essentially free of other polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

The term "isolated nucleotide sequence" as used herein refers to a nucleotide sequence which is essentially free of other nucleotide sequences, e.g., at least about 20% pure, preferably at least about 40% pure, more preferably at least about 60% pure, even more preferably at least about 80% pure, and most preferably at least about 90% pure as determined by agarose electrophoresis. The nucleotide sequence may be of genomic, cDNA, RNA, semisynthetic, synthetic origin, or any combinations thereof.

The parent microbial trypsins can also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator. Fusion proteins may also be constructed using intein technology in which fusions are created post-translationally (Cooper et al., 1993, *EMBO J.* 12: 2575-2583; Dawson et al., 1994, *Science* 266: 776-779).

Construction of Microbial Trypsin Variants with Chymotrypsin-Like Activity

In the present invention, the construction of a variant with chymotrypsin-like activity from a microbial trypsin can be accomplished by identifying the positions of the amino acids in the microbial trypsin that correspond to the amino acids of a chymotrypsin responsible for catalytic activity and substituting, deleting, and/or inserting amino acids in the microbial trypsin to correspond to the same and/or similar amino acids of the chymotrypsin by site-directed mutagenesis or any other methods known in the art. The phrase "amino acids of a chymotrypsin responsible for catalytic activity" will be understood to include not only the amino acids involved in enzyme catalysis, but also the amino acids of the binding site and surface loops of the binding pocket.

Identification of such amino acids in the microbial trypsin may be accomplished by aligning the amino acid sequence of the microbial trypsin with the amino acid sequences of one or more chymotrypsins and/or by comparing the secondary or 3D structures of the microbial trypsin and one or more chymotrypsins. It is preferable that both comparisons be performed. Thr prescursors of the microbial trypsin and chymotrypsin(s) can also be used. Essential amino acids in the parent microbial trypsin can also be identified according to other procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant variant molecules are tested for biological activity (i.e., trypsin or chymotrypsin activity) to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309:59-64.

Single or multiple amino acid substitutions can be made and tested using known methods of mutagenesis, recombination (homologous or nonhomologous), and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30: 10832-10837; U.S. Pat. No. 5,223,409; WO 92/06204) and region-directed mutagenesis (Derbyshire et al., 1986, *Gene* 46:145; Ner et al., 1988, *DNA* 7:127).

The term "shuffling" means recombination of nucleotide sequence(s) between two or more homologous nucleotide sequences resulting in recombined nucleotide sequences (i.e., nucleotide sequences having been subjected to a shuffling cycle) having a number of nucleotides exchanged, in comparison to the starting nucleotide sequences.

The term "randomized library", "variant library", or "library" is defined herein as a library of variant polypeptides. Diversity in the variant library can be generated via mutagenesis of the genes encoding the variants at the DNA triplet level, such that individual codons are variegated, e.g., by using primers of partially randomized sequence in a PCR reaction. Several techniques have been described, by which one can create a diverse combinatorial library by variegating several nucleotide positions in a gene and recombining them, for instance where these positions are too far apart to be covered by a single (spiked or doped) oligonucleotide primer. These techniques include the use of in vivo recombination of the individually diversified gene segments as described in WO 97/07205 on page 3, lines 8 to 29. They also include the use of DNA shuffling techniques to create a library of full length genes, wherein several gene segments are combined, and wherein each segment may be diversified, e.g., by spiked mutagenesis (Stemmer, 1994, *Nature* 370: 389-391; U.S. Pat. No. 5,811,238; U.S. Pat. No. 5,605,793; and U.S. Pat. No. 5,830,721). One can use a gene encoding a protein "backbone" (wild type parent polypeptide) as a template polynucleotide, and combine this with one or more single or double-stranded oligonucleotides as described in WO 98/41623 and WO 98/41622. The single-stranded oligonucleotides can be partially randomized during synthesis. The double-stranded oligonucleotides can be PCR products incorporating diversity in a specific region. In both cases, one can dilute the diversity with corresponding segments encoding the sequence of the backbone protein in order to limit the average number of changes that are introduced.

The term "recombination" is defined herein as the process wherein nucleic acids associate with each other in regions of homology, leading to interstrand DNA exchange between those sequences. For purposes of the present invention, homologous recombination is determined according to the procedures summarized by Paques and Haber, 1999, *Microbiology and Molecular Biology Reviews* 63: 349-404. "Homologous recombination" is defined herein as recombination in which no changes in the nucleotide sequences occur within the regions of homology relative to the input nucleotide sequences. For perfect homologous recombination, the regions should contain a sufficient number of nucleic acids, such as 100 to 1,500 base pairs, preferably 400 to 1,500 base pairs, and most preferably 800 to 1,500 base pairs, which are highly homologous with the corresponding nucleotide sequence to enhance the probability of homologous recombination. The recombination may also occur by non-homologous recombination. "Non-homologous recombination" is defined herein as recombination where any mode of DNA repair incorporating strand exchange results in a nucleotide sequence different from any of the recombining sequences.

Mutagenesis/shuffling methods can be combined with high-throughput, automated screening methods to detect activity of cloned, mutagenized polypeptides expressed by host cells. Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

Based on the comparative analyses described above, it is possible to construct relatively specific primers for substituting and/or deleting amino acids in the catalytic site region so new amino acids important for chymotrypsin activity are incorporated into the microbial trypsin to produce a variant enzyme with chymotrypsin-like activity. The amino acids substituted may be the same and/or similar amino acids (i.e., conservative substitutions) or different amino acids corresponding to the amino acids in the chymotrypsin. Construction of a microbial trypsin variant having chymotrypsin-like activity can be performed using such primers to PCR amplify a region or regions of DNA that encode the amino acids involved in catalytic activity, followed by DNA sequencing of the amplified PCR fragments, and assaying clones expressing the mutated nucleotide sequence.

The PCR approach to site-directed mutagenesis is based on the methods of Higuchi et at. (1988, *Nucleic Acids Research* 16: 7351). Like traditional PCR, a template is amplified using a set of gene-specific oligonucleotide primers except that one oligonucleotide, or more than one oligonucleotide in protocols that use multiple amplifications (Shimada, 1996, *Methods of Molecular Biology* 57: 157), contains the desired mutation(s). Variations include altering the hybridization site of the oligonucleotides to produce multiple, overlapping PCR fragments with the mutation in the overlap (Ho et al., 1989, *Gene* 77: 51; Horton et al., 1989, *Gene* 77: 61) and the "megaprimer" approach (Sakar and Sommer, 1990, *Bio Techniques* 8: 404), which uses three oligonucleotides and two rounds of amplification wherein a product strand from the first amplification serves as a primer in the second amplification.

A microbial trypsin variant having chymotrypsin-like activity may, for example, be constructed by site-directed mutagenesis using the following procedure: (1) aligning the microbial trypsin amino acid sequence to the amino acid sequence of a chymotrypsin; (2) based on the alignment performed in step (1), identifying the catalytic site region(s) and amino acids thereof, in the microbial trypsin sequence that correspond to the amino acids in the catalytic site region(s) of a chymotrypsin; and (3) introducing substitutions, deletions, or insertions of amino acids into the microbial trypsin so the catalytic site region corresponds to the catalytic site region of the chymotrypsin. The prescursor form of the above-noted enzymes can also be used.

The alignment in step (1) above may be performed using any of the methods known in the art. For purposes of the present invention, the degree of identity between two amino acid sequences is determined by the Clustal method (Higgins, 1989, *CABIOS* 5: 151-153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5.

For comparison of the predicted three-dimensional structures of the microbial trypsin and one or more chymotrypsins, 3D modelling programs are available (see, for example, www.accelrys.com).

Any chymotrypsin or its precursor may be used in the present invention for comparison of the amino acid sequences. The chymotrypsins are a group of conserved enzymes, in that their DNA and amino acid sequences are homologous. It is preferable that a chymotrypsin be chosen for comparison purposes such that the amino acid sequence is as closely identical to the amino acid sequence of the microbial trypsin.

In a preferred embodiment, the chymotrypsin or its precursor is bovine chymotrypsinogen A (SWISSPROT P00766), bovine chymotrypsinogen B (SWISSPROT P00767), rat chymotrypsinogen B (SWISSPROT P07338), dog chymotrypsinogen B (SWISSPROT P04813), human chymotrypsinogen B (SWISSPROT P17538), atlantic cod chymotrypsinogen (SWISSPROT P47796), or the *Fusarium oxysporum* engineered chymotrypsin of the present invention (i.e., SEQ ID NO: 4). A comparative alignment using the above noted method showed that the *Fusarium oxysporum* engineered chymotrypsin shared 36.5% identity with bovine chymotrypsin A (SWISSPROT P00766).

Construction of a microbial trypsin variant having chymotrypsin-like activity is preferably accomplished by oligonucleotide-directed mutagenesis where an oligonucleotide encoding the desired mutation(s) is annealed to one strand of a DNA which encodes the microbial trypsin and serves as a primer for initiation of DNA synthesis. The mutagenic oligonucleotide may be used to incorporate one base change or to generate multiple substitutions, insertions, and/or deletions. In situations where the amino acids to be mutated are not contiguous or semi-continguous, more than one mutagenic oligonucleotide may be necessary. Generally, a plasmid DNA containing the template of interest is denatured to produce single-stranded regions, a synthetic mutagenic oligonucleotide is annealed to the target strand, a polymerase (e.g., T4 DNA polymerase) synthesizes a new complementary strand, and finally a ligase seals the resulting nick between the end of the new strand and the mutagenic oligonucleotide.

The design of the mutagenic oligonucleotide(s) is very important for PCR efficiency. The mutagenic oligonucleotide must hybridize efficiently to the template, so there should preferably be 100% base pairing at either end of the target sequence without secondary structure formation. For small substitutions, 10-15 bases hybridizing on either side of the mismatch are usually sufficient. The composition of the 3'-end of the primer is particularly important as polymerases do not typically extend from a mismatched or poorly hybridized 3'-end. With all methods of site-directed mutagenesis, sequencing of the variant product(s) is performed to determine and confirm the nature of the identity of the mutation.

One of ordinary skill in the art will recognize that so-called conservative substitution of one amino acid residue with a similar amino acid residue is expected to produce only a minor change in the properties of the enzyme. It is routine for a person skilled in the art to identify suitable conservative substitution(s) in the microbial trypsin variants of the present invention in order to obtain other microbial trypsin variants exhibiting the same or similar properties. Similarly, the amino acids to be substituted to produce a polypeptide having chymotrypsin-like activity may involve conservative substitutions in the microbial trypsin of the corresponding amino acids in chymotrypsin. Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, *In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.*

In the present invention, amino acids 25 to 248 of SEQ ID NO: 2 of the *Fusarium oxysporum* trypsin-like protease were aligned to the amino acid sequence of bovine chymotrypsin A (SWISSPROT P00766) to ascertain the amino acids corresponding to the catalytic site amino acids of the bovine chymotrypsin. The following substitutions, deletions, and insertions of amino acids 25 to 248 of SEQ ID NO: 2 were identified based on the homology model of Hedstrom et al., 1992, *Science* 255: 1249-1253, and the modelling program Modeller according to the manufacturer's instructions (Accelrys, San Diego, Calif.), and made by PCR using mutagenic oligonucleotides: V144T, S193A, D198S, Q201M, A218I, N223S, R227S, P228T, N229S, Y230T, S231P, V192*, K197*, A226*, and G224GT.

Variants

In the present invention, the microbial trypsin variants having chymotrypsin activity comprise one or more modifications selected from the group consisting of (a) a substitution at one or more positions corresponding to positions 144, 193, 198, 201, 218, 223, 227, 228, 229, 230, and 231 of amino acids 25 to 248 of SEQ ID NO: 2, (b) a deletion at one or more positions corresponding to positions 192, 197, and 226 of amino acids 25 to 248 of SEQ ID NO: 2; and (c) an insertion between positions corresponding to positions 224 and 225 of amino acids 25 to 248 of SEQ ID NO: 2, wherein the variant, having chymotrypsin-like activity, has an amino acid sequence which has a degree of identity to amino acids 25 to 248 of SEQ ID NO: 2 (i.e., the mature polypeptide) of at least about 70%, preferably at least about 75%, more preferably at least about 80%, more preferably at least about 85%, even more preferably at least about 90%, most preferably at least about 95%, and even most preferably at least about 97% to the parent microbial trypsin. For purposes of the present invention, the degree of identity between two amino acid sequences is determined by the Clustal method (Higgins, 1989, *CABIOS* 5: 151-153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5.

The present invention also relates to isolated microbial trypsin variants having chymotrypsin-like activity, selected from the group consisting of: (a) a polypeptide having an amino acid sequence which has at least about 70%, preferably about 80%, preferably about 85%, more preferably about 90%, even more preferably about 95%, and most preferably about 97% identity to amino acids 25 to 246 of SEQ ID NO: 4; (b) a polypeptide encoded by a nucleotide sequence which hybridizes under low stringency conditions, preferably medium stringency conditions, more preferably medium-high stringency conditions, even more preferably high stringency conditions, and most preferably very high stringency conditions with (i) nucleotides 202 to 795 of SEQ ID NO: 3, (ii) a cDNA sequence of nucleotides 202 to 795 of SEQ ID NO: 3, or (iii) a complementary strand of (i) or (ii); and (c) a fragment of (a) or (b), which has chymotrypsin-like activity.

A fragment of amino acids 25 to 246 of SEQ ID NO: 4 is a polypeptide having one or more amino acids deleted from the amino and/or carboxyl terminus of this amino acid sequence. Preferably, a fragment contains at least 165 amino acid residues, more preferably at least 175 amino acid residues, and most preferably at least 185 amino acid residues.

As defined herein, an "isolated" trypsin variant having chymotrypsin-like activity is a polypeptide which is at least about 20% pure, preferably at least about 40% pure, more preferably about 60% pure, even more preferably about 80% pure, most preferably about 90% pure, and even most preferably about 95% pure, as determined by SDS-PAGE.

The present invention also relates to nucleotide sequences comprising at least one mutation in the mature polypeptide coding sequence of SEQ ID NO: 3 (i.e., nucleotides 202 to 795), in which the nucleotide sequence encodes a polypeptide which consists of amino acids 25 to 246 of SEQ ID NO: 4.

The present invention also relates to nucleotide sequences which have a degree of homology to the mature polypeptide coding sequence of SEQ ID NO: 3 (i.e., nucleotides 202 to 795) of at least about 70%, preferably about 80%, preferably about 85%, more preferably about 90%, even more preferably about 95%, and most preferably about 97% homology, which encode a variant having chymotrypsin-like activity. For purposes of the present invention, the degree of homology between two nucleotide sequences is determined by the Wilbur-Lipman method (Wilbur and Lipman, 1983, *Proceedings of the National Academy of Science USA* 80: 726-730) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=3, gap penalty=3, and windows=20.

The total number of amino acid substitutions in the variants of the present invention is preferably 11, more preferably 10, even more preferably 9, even more preferably 8, even more preferably 7, even more preferably 6, even more preferably 5, even more preferably 4, even more preferably 3, even more preferably 2, and most preferably 1.

In a preferred embodiment, the variant comprises a substitution at position 144. In a more preferred embodiment, the variant comprises a substitution at position 144 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Thr as a substitution at position 144. In a most preferred embodiment, the variant comprises the substitution V144T of amino acids 25 to 248 of SEQ ID NO: 2.

In another preferred embodiment, the variant comprises a substitution at position 193. In another more preferred embodiment, the variant comprises a substitution at position 193 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant comprises Ala as a substitution at position 193. In another most preferred embodiment, the variant comprises the substitution S193A of SEQ ID NO: 2.

In another preferred embodiment, the variant comprises a substitution at position 198. In another more preferred embodiment, the variant comprises a substitution at position 198 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant comprises Ser as a substitution at position 198. In another most preferred embodiment, the variant comprises the substitution D198S of amino acids 25 to 248 of SEQ ID NO: 2.

In another preferred embodiment, the variant comprises a substitution at position 201. In another more preferred embodiment, the variant comprises a substitution at position 201 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant comprises Met as a substitution at position 201. In another most preferred embodiment, the variant comprises the substitution Q201M of amino acids 25 to 248 of SEQ ID NO: 2.

In another preferred embodiment, the variant comprises a substitution at position 218. In another more preferred embodiment, the variant comprises a substitution at position 218 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant comprises Ile as a substitution at position 218. In another most preferred embodiment, the variant comprises the substitution A218I of amino acids 25 to 248 of SEQ ID NO: 2.

In another preferred embodiment, the variant comprises a substitution at position 223. In another more preferred embodiment, the variant comprises a substitution at position 223 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant comprises Ser as a substitution at position 223. In another most preferred embodiment, the variant comprises the substitution N223S of amino acids 25 to 248 of SEQ ID NO: 2.

In another preferred embodiment, the variant comprises a substitution at position 227. In another more preferred embodiment, the variant comprises a substitution at position 227 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant comprises Ser as a substitution at position 227. In another most preferred embodiment, the variant comprises the substitution R227S of amino acids 25 to 248 of SEQ ID NO: 2.

In another preferred embodiment, the variant comprises a substitution at position 228. In another more preferred embodiment, the variant comprises a substitution at position 228 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant comprises Thr as a substitution at position 228. In another most preferred embodiment, the variant comprises the substitution P228T of amino acids 25 to 248 of SEQ ID NO: 2.

In another preferred embodiment, the variant comprises a substitution at position 229. In another more preferred embodiment, the variant comprises a substitution at position 229 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant comprises Ser as a substitution at position 229. In another most preferred embodiment, the variant comprises the substitution N229S of amino acids 25 to 248 of SEQ ID NO: 2.

In another preferred embodiment, the variant comprises a substitution at position 230. In another more preferred embodiment, the variant comprises a substitution at position 230 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant comprises Thr as a substitution at position 230. In another most preferred embodiment, the variant comprises the substitution Y230T of amino acids 25 to 248 of SEQ ID NO: 2.

In another preferred embodiment, the variant comprises a substitution at position 231. In another more preferred embodiment, the variant comprises a substitution at position 231 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant comprises Pro as a substitution at position 231. In another most preferred embodiment, the variant comprises the substitution S231P of amino acids 25 to 248 of SEQ ID NO: 2.

In another preferred embodiment, the variant comprises one or more substitutions selected from the group consisting of V144T, S193A, D198S, Q201M, A218I, N223S, R227S, P228T, N229S, Y230T, and S231P of amino acids 25 to 248 of SEQ ID NO: 2.

In another more preferred embodiment, the variant comprises the substitutions V144T+S193A+D198S+Q201M+A218I+N223S+R227S+P228T+N229S+Y230T+S231P of amino acids 25 to 248 of SEQ ID NO: 2.

In another preferred embodiment, the variant comprises a deletion at position 192. In another more preferred embodiment, the variant comprises a deletion at position 192 of Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant comprises a deletion of Val at position 192. In another most preferred embodiment, the variant comprises the deletion V192* of amino acids 25 to 248 of SEQ ID NO: 2.

In another preferred embodiment, the variant comprises a deletion at position 197. In another more preferred embodiment, the variant comprises a deletion at position 197 of Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant comprises a deletion of Lys at position 197. In another most preferred embodiment, the variant comprises the deletion K197* of amino acids 25 to 248 of SEQ ID NO: 2.

In another preferred embodiment, the variant comprises a deletion at position 226. In another more preferred embodiment, the variant comprises a deletion at position 226 of Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant comprises a deletion of Ala at position 226. In another most preferred embodiment, the variant comprises the deletion A226* of amino acids 25 to 248 of SEQ ID NO: 2.

In another preferred embodiment, the variant comprises one or more substitutions selected from the group consisting of V144T, S193A, D198S, Q201M, A218I, N223S, R227S, P228T, N229S, Y230T, and S231P and one or more deletions selected from the group consisting of V192*, K197*, and A226* of amino acids 25 to 248 of SEQ ID NO: 2.

In another more preferred embodiment, the variant comprises the substitutions V144T+S193A+D198S+Q201M+A218I+N223S+R227S+P228T+N229S+Y230T+S231P, and the deletions V192*+K197*+A226* of amino acids 25 to 248 of SEQ ID NO: 2.

In another preferred embodiment, the variant comprises an insertion between positions 224 and 225. In another more preferred embodiment, the variant comprises an insertion between positions 224 and 225 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant comprises Thr as an insertion between positions 224 and 225. In another most preferred embodiment, the variant comprises the insertion G224GT of amino acids 25 to 248 of SEQ ID NO: 2.

In another preferred embodiment, the variant comprises one or more substitutions selected from the group consisting of V144T, S193A, D198S, Q201M, A218I, N223S, R227S, P228T, N229S, Y230T, and S231P, one or more deletions selected from the group consisting of V192*, K197*, and A226*, and optionally the insertion G224GT of amino acids 25 to 248 of SEQ ID NO: 2.

In another more preferred embodiment, the variant comprises the substitutions V144T+S193A+D198S+Q201M+A218I+N223S+R227S+P228T+N229S+Y230T+S231P, the deletions V192*+K197*+A226*, and the insertion G224GT of amino acids 25 to 248 of SEQ ID NO: 2.

In a most preferred embodiment, the variant is encoded by the nucleotide sequence contained in pEJG66.1XLGOLD which is contained in *E. coli* NRRL B-30627.

In another most preferred embodiment, the variants described above are in the form of a precursor comprising amino acids 1 to 24 of SEQ ID NO: 2 as the prepro region, or a portion thereof, linked in translation reading frame with the amino terminus of the variant.

In another most preferred embodiment, the variant comprises amino acids 25 to 246 of SEQ ID NO: 4, or a fragment thereof, which has chymotrypsin-like activity.

Nucleotide Sequences Encoding Microbial Trypsin Variants Having Chymotrypsin-Like Activity The present invention also relates to isolated nucleotide sequences which encode microbial trypsin variants having chymotrypsin-like activity obtained from a microbial trypsin, wherein the variants comprise one or more modifications selected from the group consisting of:

(1) a substitution at one or more positions corresponding to positions 144, 193, 198, 201, 218, 223, 227, 228, 229, 230, and 231 of amino acids 25 to 248 of SEQ ID NO: 2, (2) a deletion at one or more positions corresponding to positions 192, 197, and 226 of amino acids 25 to 248 of SEQ ID NO: 2; and (3) an insertion between positions corresponding to positions 224 and 225 of amino acids 25 to 248 of SEQ ID NO: 2;

wherein the microbial trypsin is (a) a polypeptide having an amino acid sequence which has at least about 70%, preferably about 80%, preferably about 85%, more preferably about 90%, even more preferably about 95%, and most preferably about 97% identity to amino acids 25 to 248 of SEQ ID NO: 2; or (b) a polypeptide encoded by a nucleotide sequence which hybridizes under low stringency conditions, preferably medium stringency conditions, more preferably medium-high stringency conditions, even more preferably high stringency conditions, and most preferably very high stringency conditions with nucleotides 202 to 801 of SEQ ID NO: 1 or its complementary strand; and wherein the variant has chymotrypsin-like activity and has an amino acid sequence that has at least 70%, preferably at least about 75%, more preferably at least about 80%, more preferably at least about 85%, even more preferably at least about 90%, most preferably at least about 95%, and even most preferably at least about 97% identity to the amino acid sequence of the microbial trypsin. The present invention also relates to nucleotide sequences encoding a microbial trypsin variant having chymotrypsin-like activity, selected from the group consisting of: (a) a nucleotide sequence encoding a polypeptide having an amino acid sequence which has at least about 70%, preferably about 80%, preferably about 85%, more preferably about 90%, even more preferably about 95%, and most preferably about 97% identity to amino acids 25 to 246 of SEQ ID NO: 4; (b) a nucleotide sequence which hybridizes under low stringency conditions, preferably medium stringency conditions, more preferably medium-high stringency conditions, even more preferably high stringency conditions, and most preferably very high stringency conditions with (i) nucleotides 202 to 795 of SEQ ID NO: 3, (ii) a cDNA sequence of nucleotides 202 to 795 of SEQ ID NO: 3, or (iii) a complementary strand of (i) or (ii); and (c) a subsequence of (a) or (b), which encodes a polypeptide fragment that has chymotrypsin-like activity.

A subsequence of SEQ ID NO: 3 is a nucleotide sequence encompassed by SEQ ID NO: 3 except that one or more nucleotides from the 5'- and/or 3'-end have been deleted. Preferably, a subsequence contains at least 495 nucleotides, more preferably at least 525 nucleotides, and most preferably at least 555 nucleotides.

A fragment of amino acids 25 to 246 of SEQ ID NO: 4 is a polypeptide having one or more amino acids deleted from the amino and/or carboxyl terminus of this amino acid sequence. Preferably, a fragment contains at least 165 amino acid residues, more preferably at least 175 amino acid residues, and most preferably at least 185 amino acid residues.

In a preferred embodiment, the isolated nucleotide sequence encodes a variant comprising a substitution at position 144. In a more preferred embodiment, the isolated nucleotide sequence encodes a variant comprising a substitution at position 144 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the isolated nucleotide sequence encodes a variant comprising Thr as a substitution at position 144. In a most preferred embodiment, the isolated nucleotide sequence encodes a variant comprising the substitution V144T of amino acids 25 to 248 of SEQ ID NO: 2.

In another preferred embodiment, the isolated nucleotide sequence encodes a variant comprising a substitution at position 193. In another more preferred embodiment, the isolated nucleotide sequence encodes a variant comprising a substitution at position 193 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the isolated nucleotide sequence encodes a variant comprising Ala as a substitution at position 193. In another most preferred embodiment, the isolated nucleotide sequence encodes a variant comprising the substitution S193A of SEQ ID NO: 2.

In another preferred embodiment, the isolated nucleotide sequence encodes a variant comprising a substitution at position 198. In another more preferred embodiment, the isolated nucleotide sequence encodes a variant comprising a substitution at position 198 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the isolated nucleotide sequence encodes a variant comprising Ser as a substitution at position 198. In another most preferred embodiment, the isolated nucleotide sequence encodes a variant comprising the substitution D198S of amino acids 25 to 248 of SEQ ID NO: 2.

In another preferred embodiment, the isolated nucleotide sequence encodes a variant comprising a substitution at position 201. In another more preferred embodiment, the isolated nucleotide sequence encodes a variant comprising a substitution at position 201 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the isolated nucleotide sequence encodes a variant comprising Met as a substitution at position 201. In another most preferred embodiment, the isolated nucleotide sequence encodes a variant comprising the substitution Q201M of amino acids 25 to 248 of SEQ ID NO: 2.

In another preferred embodiment, the isolated nucleotide sequence encodes a variant comprising a substitution at position 218. In another more preferred embodiment, the isolated nucleotide sequence encodes a variant comprising a substitution at position 218 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the isolated nucleotide sequence encodes a variant comprising Ile as a substitution at position 218. In another most preferred embodiment, the isolated nucleotide sequence encodes a variant comprising the substitution A218I of amino acids 25 to 248 of SEQ ID NO: 2.

In another preferred embodiment, the isolated nucleotide sequence encodes a variant comprising a substitution at position 223. In another more preferred embodiment, the isolated nucleotide sequence encodes a variant comprising a substitution at position 223 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the isolated nucleotide sequence encodes a variant comprising Ser as a substitution at position 223. In another most preferred embodiment, the isolated nucleotide sequence encodes a variant comprising the substitution N223S of amino acids 25 to 248 of SEQ ID NO: 2.

In another preferred embodiment, the isolated nucleotide sequence encodes a variant comprising a substitution at position 227. In another more preferred embodiment, the isolated nucleotide sequence encodes a variant comprising a substitution at position 227 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the isolated nucleotide sequence encodes a variant comprising Ser as a substitution at position 227. In another most preferred embodiment, the isolated nucleotide sequence encodes a variant comprising the substitution R227S of amino acids 25 to 248 of SEQ ID NO: 2.

In another preferred embodiment, the isolated nucleotide sequence encodes a variant comprising a substitution at position 228. In another more preferred embodiment, the isolated nucleotide sequence encodes a variant comprising a substitution at position 228 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the isolated nucleotide sequence encodes a variant comprising Thr as a substitution at position 228. In another most preferred embodiment, the isolated nucleotide sequence encodes a variant comprising the substitution P228T of amino acids 25 to 248 of SEQ ID NO: 2.

In another preferred embodiment, the isolated nucleotide sequence encodes a variant comprising a substitution at position 229. In another more preferred embodiment, the isolated nucleotide sequence encodes a variant comprising a substitution at position 229 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the isolated nucleotide sequence encodes a variant comprising Ser as a substitution at position 229. In another most preferred embodiment, the isolated nucleotide sequence encodes a variant comprising the substitution N229S of amino acids 25 to 248 of SEQ ID NO: 2.

In another preferred embodiment, the isolated nucleotide sequence encodes a variant comprising a substitution at position 230. In another more preferred embodiment, the isolated nucleotide sequence encodes a variant comprising a substitution at position 230 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the isolated nucleotide sequence encodes a variant comprising Thr as a substitution at position 230. In another most preferred embodiment, the isolated nucleotide sequence encodes a variant comprising the substitution Y230T of amino acids 25 to 248 of SEQ ID NO: 2.

In another preferred embodiment, the isolated nucleotide sequence encodes a variant comprising a substitution at position 231. In another more preferred embodiment, the isolated nucleotide sequence encodes a variant comprising a substitution at position 231 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the isolated nucleotide sequence encodes a variant comprising Pro as a substitution at position 231. In another most preferred embodiment, the isolated nucleotide sequence encodes a variant comprising the substitution S231P of amino acids 25 to 248 of SEQ ID NO: 2.

In another preferred embodiment, the isolated nucleotide sequence encodes a variant comprising one or more substitutions selected from the group consisting of V144T, S193A, D198S, Q201M, A218I, N223S, R227S, P228T, N229S, Y230T, and S231P of amino acids 25 to 248 of SEQ ID NO: 2.

In another preferred embodiment, the isolated nucleotide sequence encodes a variant comprising the substitutions V144T+S193A+D198S+Q201M+A218I+N223S+R227S+P228T+N229S+Y230T+S231P of amino acids 25 to 248 of SEQ ID NO: 2.

In another preferred embodiment, the isolated nucleotide sequence encodes a variant comprising a deletion at position 192. In another more preferred embodiment, the isolated nucleotide sequence encodes a variant comprising a deletion at position 192 of Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the isolated nucleotide sequence encodes a variant comprising a deletion of Val at position 192. In another most preferred embodiment, the isolated nucleotide sequence encodes a variant comprising the deletion V192* of amino acids 25 to 248 of SEQ ID NO: 2.

In another preferred embodiment, the isolated nucleotide sequence encodes a variant comprising a deletion at position 197. In another more preferred embodiment, the isolated nucleotide sequence encodes a variant comprising a deletion at position 197 of Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the isolated nucleotide sequence encodes a variant comprising a deletion of Lys at position 197. In another most preferred embodiment, the isolated nucleotide sequence encodes a variant comprising the deletion K197* of amino acids 25 to 248 of SEQ ID NO: 2.

In another preferred embodiment, the isolated nucleotide sequence encodes a variant comprising a deletion at position 226. In another more preferred embodiment, the isolated nucleotide sequence encodes a variant comprising a deletion at position 226 of Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the isolated nucleotide sequence encodes a variant comprising a deletion of Ala at position 226. In another most preferred embodiment, the isolated nucleotide sequence encodes a variant comprising the deletion A226* of amino acids 25 to 248 of SEQ ID NO: 2.

In another preferred embodiment, the isolated nucleotide sequence encodes a variant comprising one or more substitutions selected from the group consisting of V144T, S193A, D198S, Q201M, A218I, N223S, R227S, P228T, N229S, Y230T, and S231P, and one or more deletions selected from the group consisting of V192*, K197*, and A226* of amino acids 25 to 248 of SEQ ID NO: 2.

In another more preferred embodiment, the isolated nucleotide sequence encodes a variant comprising the substitutions V144T+S193A+D198S+Q201M+A218I+N223S+R227S+P228T+N229S+Y230T+S231P, and the deletions V192*+K197*+A226* of amino acids 25 to 248 of SEQ ID NO: 2.

In another preferred embodiment, the isolated nucleotide sequence encodes a variant comprising an insertion between positions 224 and 225. In another more preferred embodiment, the isolated nucleotide sequence encodes a variant comprising an insertion between positions 224 and 225 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the isolated nucleotide sequence encodes a variant comprising Thr as an insertion between positions 224 and 225. In another most preferred embodiment, the isolated nucleotide sequence encodes a variant comprising the insertion G224GT of amino acids 25 to 248 of SEQ ID NO: 2.

In another preferred embodiment, the isolated nucleotide sequence encodes a variant comprising one or more substitutions selected from the group consisting of V144T, S193A, D198S, Q201M, A218I, N223S, R227S, P228T, N229S, Y230T, and S231P, one or more deletions selected from the group consisting of V192*, K197*, and A226*, and optionally the insertion G224GT of amino acids 25 to 248 of SEQ ID NO: 2.

In another more preferred embodiment, the isolated nucleotide sequence encodes a variant comprising the substitutions V144T+S193A+D198S+Q201M+A218I+N223S+R227S+P228T+N229S+Y230T+S231P, the deletions V192*+K197*+ and A226*, and the insertion G224GT of amino acids 25 to 248 of SEQ ID NO: 2.

In another preferred embodiment, the isolated nucleotide sequence of the variant is set forth in SEQ ID NO: 3. In another more preferred embodiment, the isolated nucleotide sequence of the variant is the sequence contained in pEJG66.1XLGOLD which is contained in *E. coli* NRRL B-30627. In another preferred embodiment, the isolated nucleotide sequence of the variant is the mature polypeptide coding region of SEQ ID NO: 3, i.e., nucleotides 202 to 795.

In another more preferred embodiment, the isolated nucleotide sequence of the variant is the mature polypeptide coding region contained in pEJG66.1XLGOLD which is contained in *E. coli* NRRL B-30627. The present invention also encompasses nucleotide sequences which encode a polypeptide having the amino acid sequence of SEQ ID NO: 4 or the mature polypeptide thereof, which differ from SEQ ID NO: 3 by virtue of the degeneracy of the genetic code. In another preferred embodiment, the variant comprises amino acids 25 to 246 of SEQ ID NO: 4, or a fragment thereof, which has chymotrypsin-like activity. The present invention also relates to subsequences of SEQ ID NO: 3 which encode fragments of SEQ ID NO: 4 that have chymotrypsin-like activity.

In another most preferred embodiment, the nucleotide sequences described above encode variants in the form of a precursor comprising amino acids 1 to 24 of SEQ ID NO: 2 as the prepro region, or a portion thereof, linked in translation reading frame with the amino terminus of the variant.

The term "isolated nucleotide sequence" as used herein refers to a nucleotide sequence which is essentially free of other nucleotide sequences, e.g., at least about 20% pure, preferably at least about 40% pure, more preferably at least about 60% pure, even more preferably at least about 80% pure, and most preferably at least about 90% pure as determined by agarose electrophoresis.

Nucleic Acid Constructs

The present invention also relates to nucleic acid constructs comprising a nucleotide sequence encoding a a microbial trypsin variant having chymotrypsin-like activity of the present invention operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid combined and juxtaposed in a manner that would not otherwise exist in nature. The term nucleic acid construct is synonymous with the term expression cassette when the nucleic acid construct contains all the control sequences required for expression of a coding sequence of a variant of the present invention. The term "coding sequence" is defined herein as a nucleotide sequence which directly specifies the amino acid sequence of its protein product. The boundaries of a genomic coding sequence are generally determined by the ATG start codon (eukaryotes) located just upstream of the open reading frame at the 5'-end of the mRNA and a transcription terminator sequence located just downstream of the open reading frame at the -3' end of the mRNA. A coding sequence can include, but is not limited to, DNA, cDNA, and recombinant nucleotide sequences.

An isolated nucleotide sequence encoding a a microbial trypsin variant having chymotrypsin-like activity of the present invention may be manipulated in a variety of ways to provide for expression of the variant. Manipulation of the nucleotide sequence prior to its insertion into a vector may be desirable or necessary depending on the expression vector. The techniques for modifying nucleotide sequences utilizing recombinant DNA methods are well known in the art.

The term "control sequences" is defined herein to include all components which are necessary or advantageous for the expression of a a microbial trypsin variant having chymotrypsin-like activity of the present invention. Each control sequence may be native or foreign to the nucleotide sequence encoding the variant. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a a microbial trypsin variant having chymotrypsin-like activity of the present invention. The term "operably linked" is defined herein as a configuration in which a control sequence is appropriately placed at a position relative to the coding sequence of the nucleotide sequence such that the control sequence directs the expression of a a microbial trypsin variant having chymotrypsin-like activity.

The control sequence may be an appropriate promoter sequence, a nucleotide sequence which is recognized by a host cell for expression of the nucleotide sequence. The promoter sequence contains transcriptional control sequences which mediate the expression of the a microbial trypsin variant having chymotrypsin-like activity. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American,* 1980, 242: 74-94; and in Sambrook et al., 1989, supra.

Examples of suitable promoters for directing the transcription of the nucleotide constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei lipase, Aspergillus oryzae* alkaline protease, *Aspergillus oryzae* triose phosphate isomerase, *Aspergillus nidulans* acetamidase, *Fusarium venenatum* amyloglucosidase, *Fusarium oxysporum* trypsin-like protease (WO 96/00787), *Trichoderma reesei* glycoside hydrolase, *Trichoderma reesei* cellobiohydrolase I, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for

*Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1,ADH2/GAP), *Saccharomyces cerevisiae* triose phosphate isomerase (TPI), *Saccharomyces cerevisiae* metallothionine (CUP1), and *Saccharomyces cerevisiae* 3-phosphoglycerate kinase. Other useful promoters for yeast host cells are described by Romanos et al., 1992, Yeast 8: 423-488.

The control sequence may also be a suitable transcription terminator sequence, a sequence recognized by a host cell to terminate transcription. The terminator sequence is operably linked to the 3'-terminus of the nucleotide sequence encoding the a microbial trypsin variant having chymotrypsin-like activity. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C(CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5'-terminus of the nucleotide sequence encoding the a microbial trypsin variant having chymotrypsin-like activity. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polypeptide-encoding sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that codes for an amino acid sequence linked to the amino terminus of a a microbial trypsin variant having chymotrypsin-like activity and directs the encoded polypeptide into the cell's secretory pathway. The 5'-end of the coding sequence of the nucleotide sequence may inherently contain a signal peptide coding region naturally linked in translation reading frame with the segment of the coding region which encodes the secreted a microbial trypsin variant having chymotrypsin-like activity. Alternatively, the 5'-end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the a microbial trypsin variant having chymotrypsin-like activity. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* Cel145A cellulase, and *Humicola lanuginosa* lipase.

In a preferred embodiment, the signal peptide coding region is nucleotides 58 to 105 of SEQ ID NO: 1 which encode amino acids 1 to 17 of SEQ ID NO: 2.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a a microbial trypsin variant having chymotrypsin-like activity. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

In a preferred embodiment, the propeptide coding region is nucleotides 106 to 129 of SEQ ID NO: 1 which encode amino acids 18 to 24 of SEQ ID NO: 2.

Where both signal peptide and propeptide regions are present at the amino terminus of a polypeptide, the propeptide region is positioned next to the amino terminus of a polypeptide and the signal peptide region is positioned next to the amino terminus of the propeptide region.

In a preferred embodiment, the prepro coding region is nucleotides 58 to 129 of SEQ ID NO: 1 which encode amino acids 1 to 24 of SEQ ID NO: 2.

It may also be desirable to add regulatory sequences which allow the regulation of the expression of the polypeptide having chymotrypsin-like activity relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the microbial trypsin variant having chymotrypsin-like activity would be operably linked with the regulatory sequence.

Expression Vectors

The present invention also relates to recombinant expression vectors comprising a nucleotide sequence encoding a a microbial trypsin variant having chymotrypsin-like activity of the present invention, a promoter, and transcriptional and translational stop signals. The various nucleotide and control sequences described above may be joined together to produce a recombinant expression vector which may include one or more convenient restriction sites to allow for insertion or substitution of the nucleotide sequence encoding the variant at such sites. Alternatively, the nucleotide sequence may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is distinct from chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus.*

The vectors of the present invention preferably contain an element(s) that permits integration of the vector into the host cell's genome or autonomous replication of the vector in the cell independent of the genome.

For integration into the host cell genome, the vector may rely on the nucleotide sequence encoding the variant or any other element of the vector for integration of the vector into the genome by homologous or nonhomologous recombination. Alternatively, the vector may contain additional nucleotide sequences for directing integration by homologous recombination into the genome of the host cell. The additional nucleotide sequences enable the vector to be integrated into the host cell genome at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes functioning temperature-sensitive in the host cell (see, e.g., Ehrlich, 1978, *Proceedings of the National Academy of Sciences USA* 75: 1433). Examples of a plasmid replicator useful in a filamentous fungal cell are AMA1 and ANS1 (Gems et al., 1991, *Gene* 98:61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a nucleotide sequence of the present invention may be inserted into the host cell to increase production of the gene product. An increase in the copy number of the nucleotide sequence can be obtained by integrating at least one additional copy of the sequence into the host cell genome or by including an amplifiable selectable marker gene with the nucleotide sequence where cells containing amplified copies of the selectable marker gene, and thereby additional copies of the nucleotide sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleotide sequence encoding a a microbial trypsin variant having chymotrypsin-like activity, which are advantageously used in the recombinant production of the variant. A vector comprising a nucleotide sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular cells are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, and *Bacillus thuringiensis*; or a *Streptomyces* cell, e.g., *Streptomyces lividans* and *Streptomyces murinus*, or gram negative bacteria such as *E. coli* and *Pseudomonas* sp. In a preferred embodiment, the bacterial host cell is a *Bacillus lentus, Bacillus licheniformis, Bacillus stearothermophilus*, or *Bacillus subtilis* cell. In another preferred embodiment, the *Bacillus* cell is an alkalophilic *Bacillus*.

The introduction of a vector into a bacterial host cell may, for instance, be effected by protoplast transformation (see, e.g., Chang and Cohen, 1979, Molecular General Genetics 168: 111-115), using competent cells (see, e.g., Young and Spizizin, 1961, Journal of Bacteriology 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may be any eukaryote, such as a mammalian, insect, plant, or fungal cell.

The host cell may be any fungal cell. "Fungi" as used herein includes the phyla Ascomycota, Basidiomycota, Chytridiomycota, and Zygomycota (as defined by Hawksworth et al., *In, Ainsworth and Bisby's Dictionary of The Fungi,* 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In a more preferred embodiment, the yeast host cell is a *Candida, Hansenula, Kluyveromyces, Pichia, Saccharomyces, Schizosaccharomyces*, or *Yarrowia* cell.

In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In a more preferred embodiment, the filamentous fungal host cell is, but not limited to, an *Acremonium, Aspergillus, Fusarium, Humicola, Mucor, Myceliophthora, Neurospora, Penicillium, Thielavia, Tolypocladium*, or *Trichoderma* cell.

In a most preferred embodiment, the filamentous fungal host cell is an *Aspergillus awamori, Aspergillus foetidus, Aspergillus japonicus, Aspergillus nidulans, Aspergillus niger* or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* cell. In an even most preferred embodiment, the filamentous fungal parent cell is a *Fusarium venenatum* (Nirenberg sp. nov.) cell. In another most preferred embodiment, the filamentous fungal host cell is a *Humicola insolens, Humicola lanuginosa, Mucor miehei, Myceliophthora thermophila, Neurospora crassa, Penicillium purpurogenum, Thielavia terrestris, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a variant having chymotrypsin-like activity, comprising:

(a) cultivating a host cell under conditions suitable for the expression of the variant, wherein the host cell comprises a nucleotide sequence which comprises one or more modifications selected from the group consisting of:

(1) a substitution at one or more positions corresponding to positions 144, 193, 198, 201, 218, 223, 227, 228, 229, 230, and 231 of amino acids 25 to 248 of SEQ ID NO: 2,
(2) a deletion at one or more positions corresponding to positions 192, 197, and 226 of amino acids 25 to 248 of SEQ ID NO: 2; and
(3) an insertion between positions corresponding to positions 224 and 225 of amino acids 25 to 248 of SEQ ID NO: 2; and
(b) recovering the variant from the cultivation medium.

In the production methods of the present invention, the host cells are cultivated in a nutrient medium suitable for production of the a microbial trypsin variant having chymotrypsin-like activity using methods known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

In an alternative embodiment, the a microbial trypsin variant having chymotrypsin-like activity is not recovered, but rather a host cell of the present invention expressing the variant is used as a source of the variant.

The microbial trypsin variant having chymotrypsin-like activity may be detected using methods known in the art that are specific for the polypeptides. These detection methods may include use of specific antibodies, formation of an enzyme product, or disappearance of an enzyme substrate. For example, an enzyme assay with N-succinyl-Ala-Ala-Pro-Phe p-nitroanilide as substrate may be used to determine the chymotrypsin-like activity of the variant, as described herein.

The resulting a microbial trypsin variant having chymotrypsin-like activity may be recovered by methods known in the art. For example, the polypeptide may be recovered from the nutrient medium by conventional procedures including, but not limited to, collection, centrifugation, filtration, extraction, spray-drying, evaporation, or precipitation.

A a microbial trypsin variant having chymotrypsin-like activity of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

An defined herein, an "isolated" variant is a polypeptide which is at least about 20% pure, preferably at least about 40% pure, more preferably about 60% pure, even more preferably about 80% pure, most preferably about 90% pure, and even most preferably about 95% pure, as determined by SDS-PAGE. The term "isolated" variant may alternatively be termed "purified" variant.

Applications

The microbial trypsin variants having chymotrypsin-like activity of the present invention may be used in a number of industries including the detergent, leather, chemical, agricultural, pharmaceutical, food, and dairy industries. For example, the polypeptides may be used as a component of a detergent composition as described, for example, in U.S. Pat. Nos. 5,288,627, 5,693,520 and 5,948,746. The polypeptides may also be used in numerous applications in the food industry as described, for example, in Owen R. Fennema, ed., in *Food Chemistry, Marcel Dekker, Inc., New York*, 1985. The polypeptides may also be used as a bating enzyme in the leather industry. The polypeptides may be further used in cheese making as described, for example, in U.S. Pat. No. 5,948,746.

This summary is not in any way intended to be a complete list of suitable applications of the trypsin variants having chymotrypsin-like activity of the present invention. The trypsin variants of the present invention may be used in other industrial applications known in the art.

Detergent Compositions

The variants of the present invention may be added to and thus become a component of a detergent composition.

The detergent composition of the present invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the present invention provides a detergent additive comprising the enzyme of the invention. The detergent additive as well as the detergent composition may comprise one or more other enzymes such as a protease, lipase, cutinase, an amylase, carbohydrase, cellulase, pectinase, mannanase, arabinase, galactanase, xylanase, oxidase, e.g., a laccase, and/or peroxidase.

In general the properties of the chosen enzyme(s) should be compatible with the selected detergent, (i.e., pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metalloprotease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g., of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Preferred commercially available protease enzymes include Alcalase™, Savinase™, Primase™, Duralase™, Esperase™, and Kannase™ (Novo Nordisk A/S), Maxatase™, Maxacal™ Maxapem™, Properase™, Purafect™, Purafect OxP™, FN2™, and FN3™ (Genencor International Inc.).

Lipases: Suitable lipases include those of bacterial or fungal origin. Chemically modified or protein engineered mutants are included. Examples of useful lipases include lipases from *Humicola* (synonym *Thermomyces*), e.g., from

*Humicola lanuginosa* (*Thermomyces lanuginosus*) as described in EP 258 068 and EP 305 216 or from *Humicola insolens* as described in WO 96/13580, a *Pseudomonas lipase*, e.g., from *Pseudomonas alcaligenes* or *Pseudomonas pseudoalcaligenes* (EP 218 272), *Pseudomonas cepacia* (EP 331 376), *Pseudomonas stutzeri* (GB 1,372,034), *Pseudomonas fluorescens, Pseudomonas* sp. strain SD 705 (WO 95/06720 and WO 96/27002), *Pseudomonas wisconsinensis* (WO 96/12012), a *Bacillus lipase*, e.g., from *Bacillus subtilis* (Dartois et al., 1993, *Biochemica et Biophysica Acta,* 1131, 253-360), *Bacillus stearothermophilus* (JP 64/744992) or *Bacillus pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipolase™ and Lipolase Ultra™ (Novo Nordisk A/S).

Amylases: Suitable amylases ($\alpha$ and/or $\beta$) include those of bacterial or fungal origin. Chemically modified or protein engineered mutants are included. Amylases include, for example, $\alpha$-amylases obtained from *Bacillus*, e.g., a special strain of *Bacillus licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl™, Termamyl™, Fungamyl™ and BAN™ (Novo Nordisk A/S), Rapidase™ and Purastar™ (from Genencor International Inc.).

Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Commercially available cellulases include Celluzyme™, and Carezyme™ (Novo Nordisk A/S), Clazinase™, and Puradax HA™ (Genencor International Inc.), and KAC-500 (B)™ (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g., from *Coprinus cinereus*, and variants thereof as those described in WO 93/24618, WO 95/10602, and WO 98/15257.

Commercially available peroxidases include Guardzyme™ (Novo Nordisk A/S).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g., SKS-6 from Hoechst).

The detergent may comprise one or more polymers. Examples are carboxymethylcellulose, poly(vinylpyrrolidone), poly (ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of, for example, the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, for example, WO 92/19709 and WO 92/19708.

The detergent may also contain other conventional detergent ingredients such as, e.g., fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, in particular the enzyme of the invention, may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

The enzyme of the invention may additionally be incorporated in the detergent formulations disclosed in WO 97/07202 which is hereby incorporated as reference.

The present invention is further described by the following examples which should not be construed as limiting the scope of the invention.

EXAMPLES

Materials

Chemicals used as buffers and substrates were commercial products of at least reagent grade. N-Succinyl-Ala-Ala-Pro-Phe-p-nitroanilide, N-succinyl-Ala-Ala-Pro-Leu-p-nitroanilide, N-$\alpha$-benzoyl-DL-arginine-p-nitroanilide, and beta-lactoglobulin A were obtained from Sigma Chemicals (St Louis, Mo.). All primers were synthesized by MWG, High Point, N.C.

Media and Solutions

VNO3RLMT was composed per liter of 20 ml of 50× Vogels-24 mM $NaNO_3$, 273.33 g of sucrose, and 15 g of LMT Agarose.

50× Vogel's was composed per liter of 125 g of sodium citrate, 250 g of $KH_2PO_4$, 106.25 g of $NaNO_3$, 10 g of $MgSO_4.7H_2O$, 5 g of $CaCl_2.2H_2O$, 2.5 ml of biotin stock solution (5 mg of biotin in 100 ml of 50% ethanol), and 5 ml of Vogels trace element solution.

Vogels trace element solution was composed per liter of 50 g of citric acid, 50 g of $ZnSO_4.7H_2O$ (or 2.4 g of $ZnCl_2$), 10 g of $Fe(NH_4)_2(SO_4)_2.6H_2O$ (or 0.68 g of $FeCl_3$), 2.5 g of $CuSO_4.5H_2O$, 0.5 g of $MnSO_4.H_2O$, 0.5 g of $H_3BO_3$, and 0.5 g of $Na_2MoO_4.2H_2O$ (or $(NH_4)_2MoO_4$).

RA sporulation medium was composed per liter of 50 g of succinic acid, 12.1 g of $NaNO_3$, 1 g of glucose, 20 ml of 50× Vogels, and 0.5 ml of a 10 mg/ml $NaMoO_4$ stock solution, pH to 6.0.

YEPG medium was composed per liter of 10 g of yeast extract, 20 g of peptone, and 20 g of glucose.

STC was composed of 0.8 M sorbitol, 25 mM Tris pH 8, and 25 mM $CaCl_2$.

SPTC was composed of 40% PEG 4000, 0.8 M sorbitol, 25 mM Tris pH 8, and 25 mM $CaCl_2$.

M400 medium was composed per liter of 50 g of maltodextrin, 2 g of $MgSO_4.7H_2O$, 2 g of $KH_2PO_4$, 4 g of citric acid, 8 g of yeast extract, 2 g of urea, 0.5 g of $CaCl_2$, and 0.5 ml of AMG trace metals solution.

AMG trace metals solution was composed per liter of 14.3 g of $ZnSO_4.7H_2O$, 2.5 g of $CuSO_4.5H_2O$, 0.5 g of $NiCl_2$, 13.8 g of $FeSO_4$, 8.5 g of $MnSO_4$, and 3.0 g of citric acid.

Example 1

Engineering of *Fusarium oxysporum* Trypsinogen-Like Gene

The DNA sequence of the *Fusarium oxysporum* trypsinogen-like gene (SEQ ID NO: 1) and the deduced amino acid sequence thereof (SEQ ID NO: 2) are shown in FIG. 1.

The *Fusarium oxysporum* trypsinogen-like gene (SEQ ID NO: 1) was mutagenized to include 11 amino acids substitutions, 3 amino acid deletions, and 1 amino acid insertion (FIG. 2, SEQ ID NOs: 3 and 4) based on the homology model of Hedstrom et al., 1992, *Science* 255: 1249-1253, and modeling program Modeller of Accelrys, San Diego, Calif., with the X-ray structure of the *Fusarium oxysporum* trypsin-like protein (Rypniewski et al., 1993, *Protein Engineering* 6: 341-348), which comparatively aligned the amino acid sequences of a *Fusarium oxysporum* trypsin and bovine chymotrypsin A. FIG. 3 shows a comparative alignment of the amino acid sequences of a *Fusarium oxysporum* trypsin, bovine chymotrypsin A, and *Fusarium oxysporum* trypsin-like enzyme engineered to a polypeptide having chymotrypsin-like activity.

Plasmid pJRoy75 (FIG. 4) was constructed by performing a three-way ligation between the following three fragments: (1) A 5344 by fragment liberated by digestion of pRaMB60 (WO 00/56900) with Pme I and Nhe I. This fragment harbored the 3'-end of the *Fusarium oxysporum* trypsinogen-like gene terminator, the *Streptomyces hygroscopicus* bar gene (driven by the *Aspergillus nidulans* amdS promoter and the *Aspergillus niger* AMG terminator), and the ori region for replication of the plasmid. (2) A 1255 by fragment liberated by digestion of pJRoy5 or pJRoy 6 with Nco I and Nhe I (U.S. Pat. No. 5,837,847). Plasmid pJRoy5 was identical to pJRoy6 except that the orientation of the *Fusarium oxysporum* trypsinogen-like gene was reversed. This fragment harbored the *Fusarium oxysporum* trypsinogen-like open reading frame (ORF) and the 5' region of the *Fusarium oxysporum* trypsinogen-like gene terminator. (3) A 2115 by fragment liberated by digestion of pRaMB62 (WO 00/56900) with Stu I and BspLU11 I. This fragment harbored the *Fusarium* venenatum AMG promoter. The desired ligation product was confirmed by restriction enzyme digest analysis and DNA sequencing and designated pJRoy75 (FIG. 4).

Plasmid pJRoy75 was used as the source of the trypsinogen-like gene. The substitutions made in the *Fusarium oxysporum* trypsin gene were V144T, S193A, D198S, Q201M, A218I, N223S, R227S, P228T, N229S, Y230T, and S231P. Residues V192, K197, and A226 were deleted. A Thr was inserted between G224 and C225.

A Quick Change Site Directed Mutagenesis Kit (Stratagene, Los Angeles, Calif.) was used, according to the manufacturer's instructions, to create a single amino acid change at codon 144 from valine to threonine. The following primers were used to produce the valine to threonine change, where the mutations are in bold.

Upper 991056:

(SEQ ID NO: 5)
GGATCTTCTGCCACTACTGCTGGCTGGTAAGTCG

Lower 991057:

(SEQ ID NO: 6)
CGACTTACCAGCCAGCAGTAGTGGCAGAAGATCC

The mutagenesis reaction contained 5 μl of 10× reaction buffer (Stratagene, Los Angeles, Calif.), 1 μl of pJROY75 (155 ng/μl), 1 μl of primer 991056 (250 ng/μl), 1 μl of primer 991057 (250 ng/μl), 2 μl of dNTPs (10 mM), 37.5 μl of deionized water, 2.5 μl of DMSO, and 1 μl of Pfu DNA polymerase. The resulting plasmid was designated pMUT1. One μl of the mutagenesis reaction was used to transform 50 μl of XL1Blue cells (Stratagene, Los Angeles, Calif.). Eight of the transformed colonies were picked individually to 3 ml of LB medium supplemented with 100 μg of ampicillin per ml and grown overnight at 37° C., 250 rpm. Miniprep DNA was extracted from these clones using the Biorobot 9600 (Qiagen, Valencia, Calif.). The PCR product was then sequenced to confirm the presence of the mutations. DNA sequencing was performed with an ABI Prism 3700 DNA Analyzer, 3700 Data Collection Software version 1.1, and Data Extractor Sequencing Analysis Software version 3.6, with analysis module BC-POPS opt.saz (Perkin Elmer, Applied Biosystems, Foster City. CA). Lac-forward and lac-reverse primers were used with dye-terminator chemistry (Giesecke et al., 1992, *Journal of Virol. Methods* 38: 47-60).

Plasmid MUT1 was then mutagenized at the termination signal sequence of the *Fusarium oxysporum* trypsin-like gene to contain a 3' Pac I site using the Quick Change Site-Directed Mutagenesis Kit according to the manufacturer's protocols. The following primers were used to introduce a 3' Pac I site:

Upper 991058:

(SEQ ID NO: 7)
GACACCTATGCTTAATTAATACCTTGTTGGAAGCGTCGAGATG

Lower 991059:

(SEQ ID NO: 8)
CATCTCGACGCTTCCAACAAGGTATTAATTAAGCATAGGTGTC

The reaction contained 5 μl of 10× reaction buffer (Stratagene, Los Angeles, Calif.), 2 μl of pMUT1 (200 ng/μl), 1.7 μl of primer 991059 (250 ng/μl), 1.7 μl of primer 991058 (250 ng/μl), 2 μl of dNTPs (10 mM), 35.1 μl of deionized water, 2.5 μl of DMSO, and 1 μl of Pfu DNA polymerase. The resulting plasmid was isolated as described above and designated pMUT2.

Plasmid pMUT2 differed from pJRoy75 in that two base pairs were changed within the *Fusarium oxysporum* trypsin-like gene coding region (thereby changing a single amino acid from valine to threonine), and a Pac I site was at the 3'-end of the coding sequence. Plasmid MUT2 also contained an internal SacI site in the *Fusarium oxysporum* trypsin gene coding region (as in pJRoy75) just upstream of the region to be replaced by a synthetic fragment containing the remaining mutations.

The remaining mutations were introduced by mutagenizing the 3' portion of the gene with a 200 by synthetic DNA fragment. To assemble the 200 by fragment, six primers ranging in size from 57-81 bases were designed based on a *Fusarium* codon usage table shown in Table 1 to incorporate the appropriate mutations. All of the primers, except the 5'-upper (primer 991050) and the 3'-lower (primer 991055), were phosphorylated, annealed and ligated. The primers used to assemble the fragment are shown below:

Primer 991050 (Upper):

(SEQ ID NO: 9)
AGTACGGCACCTCCGCCATCACCAACCAGATGTTCTGTGCTGGTGCTTCC
GGTGGCTCTTCTTGCATGGGTGAC

Primer 991051 (Upper):

(SEQ ID NO: 10)
AGCGGCGGCCCCATCGTCGACAGCTCCAACACTCTTATCGGTATCGTCTC
TTGGGGTTCTGGAACTTGTTCTAC

Primer 991052 (Upper):

(SEQ ID NO: 11)
TTCTACTCCTGGTGTCTATGCCAGCGTTGGTGCTCTCCGCTCTTTCATTG
ACACCTATGCTTAA

Primer 991053 (Upper):

(SEQ ID NO: 12)
TTAAGCATAGGTGTCAATGAAAGAGCGGAGAGCACCAACGCTGGCATAGA
CACCAGGAGTAGAAGTAGAACAAGTTCCAGA

Primer 991054 (Lower):

(SEQ ID NO: 13)
ACCCCAAGAGACGATACCGATAAGAGTGTTGGAGCTGTCGACGATGGGGC
CGCCGCTGTCACCCATGCAAGAAG

Primer 991055 (Lower):

(SEQ ID NO: 14)
AGCCACCGGAAGCACCAGCACAGAACATCTGGTTGGTGATGGCGGAGGTG
CCGTAT

TABLE 1

| *Fusarium venenatum* Codon usage | | | | | | | | | | | | | | |
|---|---|---|---|---|---|---|---|---|---|---|---|---|---|---|
| gca | Ala(A) | 125 | # | cag | Gln(Q) | 183 | # | uug | Leu(L) | 98 | # | uaa | Ter(.) | 6 |
| gcc | Ala(A) | 213 | # | --- | Gln(Q) | 352 | # | --- | Leu(L) | 670 | # | uag | Ter(.) | 5 |
| gcg | Ala(A) | 110 | # | gaa | Glu(E) | 157 | # | aaa | Lys(K) | 99 | # | uga | Ter(.) | 2 |
| gcu | Ala(A) | 239 | # | gag | Glu(E) | 249 | # | aag | Lys(K) | 290 | # | --- | Ter(.) | 13 |
| --- | Ala(A) | 687 | # | --- | Glu(E) | 406 | # | --- | Lys(K) | 389 | # | aca | Thr(T) | 132 |
| aga | Arg(R) | 51 | # | gga | Gly(G) | 125 | # | aug | Met(M) | 178 | # | acc | Thr(T) | 151 |
| agg | Arg(R) | 24 | # | ggc | Gly(G) | 193 | # | --- | Met(M) | 178 | # | acg | Thr(T) | 61 |
| cga | Arg(R) | 92 | # | ggg | Gly(G) | 46 | # | uuc | Phe(F) | 208 | # | acu | Thr(T) | 171 |
| cgc | Arg(R) | 91 | # | ggu | Gly(G) | 231 | # | uuu | Phe(F) | 116 | # | --- | Thr(T) | 515 |
| cgg | Arg(R) | 34 | # | --- | Gly(G) | 595 | # | --- | Phe(F) | 324 | # | ugg | Trp(W) | 101 |
| cgu | Arg(R) | 84 | # | cac | His(H) | 105 | # | cca | Pro(P) | 107 | # | --- | Trp(W) | 101 |
| --- | Arg(R) | 376 | # | cau | His(H) | 81 | # | ccc | Pro(P) | 139 | # | uac | Tyr(Y) | 165 |
| aac | Asn(N) | 258 | # | --- | His(H) | 186 | # | ccg | Pro(P) | 45 | # | uau | Tyr(Y) | 71 |
| aau | Asn(N) | 118 | # | aua | Ile(I) | 29 | # | ccu | Pro(P) | 144 | # | --- | Tyr(Y) | 236 |
| --- | Asn(N) | 376 | # | auc | Ile(I) | 237 | # | --- | Pro(P) | 435 | # | gua | Val(V) | 49 |
| gac | Asp(D) | 259 | # | auu | Ile(I) | 182 | # | agc | Ser(S) | 84 | # | guc | Val(V) | 235 |
| gau | Asp(D) | 265 | # | --- | Ile(I) | 448 | # | agu | Ser(S) | 72 | # | gug | Val(V) | 93 |
| --- | Asp(D) | 524 | # | cua | Leu(L) | 50 | # | uca | Ser(S) | 109 | # | guu | Val(V) | 191 |

TABLE 1-continued

| *Fusarium venenatum* Codon usage | | | | | | | | | | | |
|---|---|---|---|---|---|---|---|---|---|---|---|
| ugc | Cys(C) | 48 # | cuc | Leu(L) | 207 # | ucc | Ser(S) | 120 # | --- | Val(V) | 568 |
| ugu | Cys(C) | 47 # | cug | Leu(L) | 106 # | ucg | Ser(S) | 77 # | nnn | ???(X) | 0 |
| --- | Cys(C) | 95 # | cuu | Leu(L) | 185 # | ucu | Ser(S) | 148 # | TOTAL | | 8084 |
| caa | Gln(Q) | 169 # | uua | Leu(L) | 24 # | --- | Ser(S) | 610 # | | | |

Primers 991051, 991052, 991053, and 991054 were phosphorylated in individual reactions in which 1 μl of each primer (50 pm/μl), 2 μl (10 units/μl) of T4 polynucleotide kinase (NEBiolabs, Beverly, Mass.), 2 μl of 10× kinase buffer, and 15 μl of deionized water were incubated at 37° C. for 30 minutes, then at 65° C. for 20 minutes. All the primers, 991050, 991051, 9901052, 991053, 991054, and 991055, were then annealed and ligated. One μl of each oligonucleotide and 4 μl of deionized water were heated to 100° C. for 3 minutes and cooled to room temperature over a period of 1 hour. Then 2 μl of 10× ligase buffer, 7 μl of deionized water, and 1 μl of T4 ligase (Roche, Indianapolis, Ind.) were added and the reaction was incubated overnight at room temperature.

The ligation product was purified using the Qiaquick Nucleotide Purification Kit (Qiagen, Valencia, Calif.) according to the manufacturer's protocol using 30 μl of EB (Qiagen, Valencia, Calif.) for elution. The purified product was then used as the template in a PCR reaction to generate a 5' Sac I site and a 3' Pac I site, which were necessary to ligate the fragment into pMUT2. The following primers were used.

```
Primer 991063 (Upper):
CCCGAGCTCAGTACGGCACCTCCG      (SEQ ID NO: 15)

Primer 991064 (Lower):
CCCTTAATTAAGCATAGGTGTC        (SEQ ID NO: 16)
```

The PCR reaction contained 5 μl of 10× Pwo polymerase buffer, 3 μl of 10 mM dNTPs, 1 μl of primer 991063 (50 pm/μl), 1 μl of primer 991064 (50 pm/μl), 9 μl of deionized water, and 1 μl of Pwo DNA polymerase (Roche, Indianapolis, Ind.). The amplifications were incubated in a Perkin Elmer 480 Thermal Cycler programmed for 1 cycle at 94° C. for 2 minutes; 10 cycles each at 94° C. for 30 seconds, and 55° C. for 45 seconds, and 72° C. for 1 minute; 25 cycles each at 94° C. for 30 seconds, 37° C. for 30 seconds, and 72° C. for 1 minute; 17 cycles each at 94° C. for 30 seconds, 55° C. for 45 seconds, and 72° C. for 1 minute with a 20 second per cycle extension; and a final 72° C. extension for 10 minutes and a soak cycle at 4° C. One μl of Taq polymerase (5 units/0), (Roche, Brangburt, N.J.) was then added to create A overhangs, and the reaction was incubated at 72° C. for 10 minutes. The reaction was then purified using the Qiaquick PCR Clean Up Kit (Qiagen, Valencia, Calif.).

The PCR product was then cloned into the TOPO TA vector pCR2.1-TOPO (Invitrogen, Carlsbad, Calif.) and transformed into *E. coli* TOP10 cells (Invitrogen, Carlsbad, Calif.). Eight of the transformed *E. coli* Top10 colonies were picked individually to 3 ml of LB medium supplemented with 100 μg of ampicillin per ml and grown overnight at 37° C., 250 rpm. Miniprep DNA was extracted from these clones using the Biorobot 9600 (Qiagen, Valencia, Calif.). The PCR product was then sequenced to confirm the presence of the mutations. DNA sequencing was performed with an ABI Prism 3700 DNA Analyzer, 3700 Data Collection Software version 1.1, and Data Extractor Sequencing Analysis Software version 3.6, with analysis module BC-POPS opt.saz (Perkin Elmer, Applied Biosystems, Foster City. CA). Lac-forward and lac-reverse primers were used with dye-terminator chemistry in the sequencing (Giesecke et al., 1992, supra).

The DNA sequence of the *Fusarium oxysporum* trypsin-like gene engineered to encode a polypeptide having chymotrypsin-like activity (SEQ ID NO: 3) and the deduced amino acid sequence thereof (SEQ ID NO: 4) is shown in FIG. 2. A comparative alignment of chymotrypsin sequences was undertaken using the Clustal method (Higgins, 1989, CABIOS 5: 151-153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5.

The comparative alignment showed that the *Fusarium oxysporum* trypsin-like enzyme engineered to a polypeptide having chymotrypsin-like activity shared 6.5% identity with bovine chymotrypsin A (SWISSPROT P00766).

Example 2

Construction of Plasmid pEJG66

A TOPO TA-generated clone containing the correct sequence (Example 1) was digested with SacI and PacI and the resulting 200 base pair fragment was purified using a Qiaquick Gel Extraction Kit (Qiagen, Valencia, Calif.). Plasmid pMUT2 was digested with SpeI and PacI and the resulting 5823 base pair fragment was purified using a Qiaquick Gel Extraction Kit. Plasmid pMUT2 was also digested with SpeI and SacI and the resulting 2673 base pair fragment was purified using Qiaquick Gel Extraction Kit.

Figure 5:
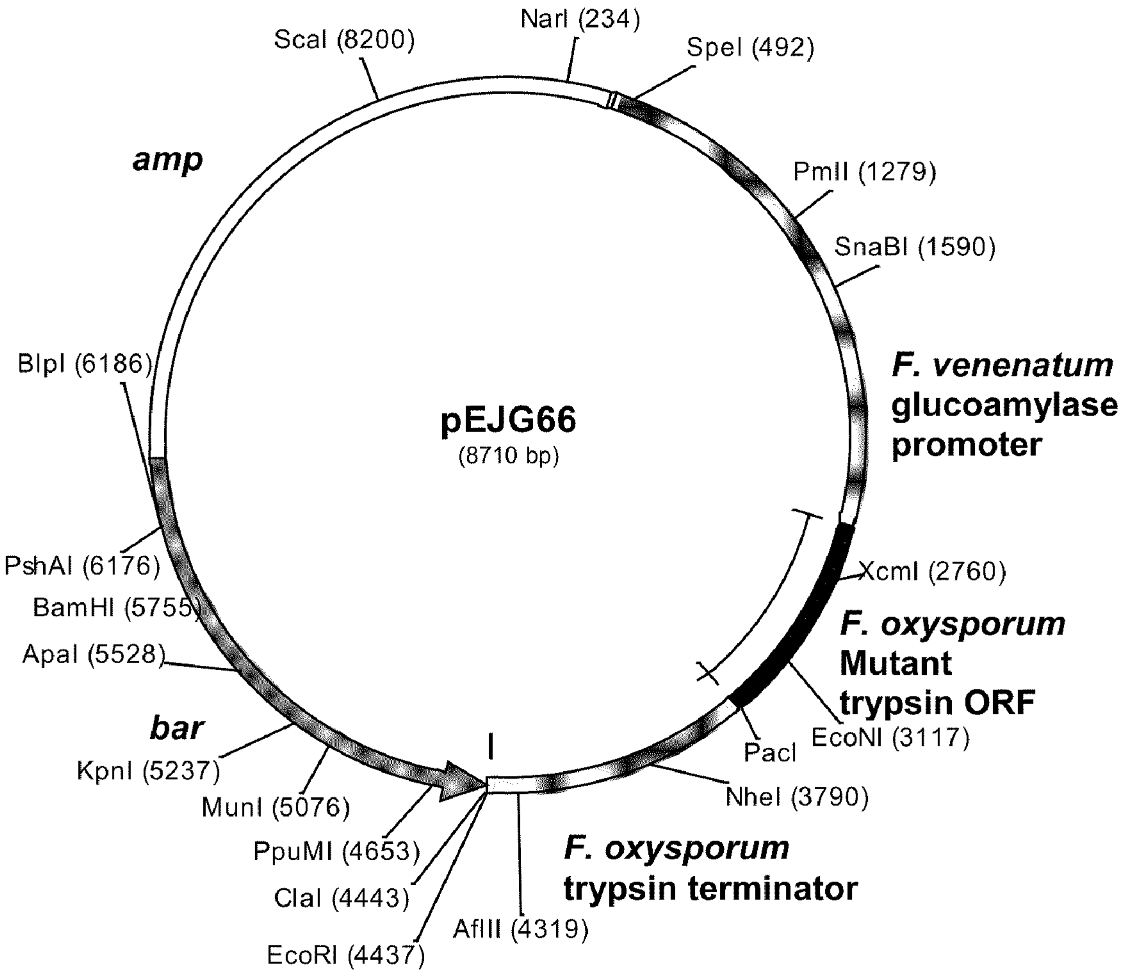
FIG. 5 shows a restriction map of pEJG66.

The pMUT2 SpeI/PacI 5823 base pair fragment, pMUT2 SpeI/SacI 2673 base pair fragment, and 200 base pair synthetic SacI/PacI fragment were ligated together to create pEJG66 (FIG. 5). pEJG66 was comprised of a *Fusarium venenatum* AMG promoter (WO 00/56900) driving expression of the chymotrypsin-like gene, the *Fusarium oxysporum* trypsin-like gene terminator, and a bar gene (*Streptomyces hydroscopicus* phosphinothricin acetyltransferase) for selection.

*E. coli* XL10 Gold Solopack (Stratagene, Los Angeles, Calif.) was transformed with pEJG66. Twenty four individual colonies were then picked into 3 ml of LB medium supplemented with 100 μg of ampicillin per ml and grown overnight shaking at 250 rpm at 37° C. Miniprep DNA was extracted from these clones using the Qiagen Biorobot 9600 according to the manufacturer's protocols. DNA from one clone, designated *E. coli* pEJG66.1XLGOLD, was then sequenced, which confirmed the presence of the mutations. DNA sequencing was performed with an ABI Prism 3700 DNA Analyzer, 3700 Data Collection Software version 1.1, and Data Extractor Sequencing Analysis Software version 3.6, with analysis module BC-POPS opt.saz (Perkin Elmer, Applied Biosystems, Foster City, Calif.) The primers below were used with dye-terminator chemistry (Giesecke et al., 1992, supra):

```
991072:
TTCATATTCAATTTGGGCTAT    (SEQ ID NO: 17)

991070:
TATCTCAGATGTCAGAGAACG    (SEQ ID NO: 18)

991069:
ATGGTCAAGTTCGCTTCCGTC    (SEQ ID NO: 19)

991071:
GCTCTGACCCTGTCGCTGGAT    (SEQ ID NO: 20)

991074:
CTGCCAACATAGATAATGAGG    (SEQ ID NO: 21)

991073:
GTTGGATCTTAGTCCTGGTTG    (SEQ ID NO: 22)

990904:
ATCCAAGACTCAAGCTAGAGA    (SEQ ID NO: 23)
```

*E. coli* pEJG66.1XLGOLD was deposited on Sep. 6, 2002, with the Agricultural Research Service Patent Culture Collection, Northern Regional Research Center, 1815 University Street, Peoria, Ill., 61604, and given the accession number NRRL B-30627.

Example 3

Transformation of *Fusarium venenatum* with pEJG66

*Fusarium venenatum* (Δtri5, Δdps1) was obtained as described in WO 00/42203. Spores of *Fusarium venenatum* (Δtri5, Δdps1) were generated by inoculating a flask containing 500 ml of RA sporulation medium with 10 plugs from a 1× Vogels medium plate (2.5% Noble agar) supplemented with 2.5% glucose and 2.5 mM sodium nitrate and incubating at 28° C., 150 rpm for 2 to 3 days. Spores were harvested through MIRACLOTH™ (Calbiochem, San Diego, Calif.) and centrifuged for 20 minutes at 7000 rpm in a Sorvall RC-5B centrifuge (E. I. DuPont De Nemours and Co., Wilmington, Del.). Pelleted spores were washed twice with sterile distilled water, resuspended in a small volume of water, and then counted using a hemocytometer.

Protoplasts were prepared by inoculating 100 ml of YEPG medium with $4\times10^7$ spores of *Fusarium venenatum* (Δtri5, Δdps1) and incubating for 16 hours at 24° C. and 150 rpm. The culture was centrifuged for 7 minutes at 3500 rpm in a Sorvall RT 6000D (E. I. DuPont De Nemours and Co., Wilmington, Del.). Pellets were washed twice with 30 ml of 1 M $MgSO_4$ and resuspended in 15 ml of 5 mg/ml of NOVOZYME 234™ (batch PPM 4356, Novo Nordisk A/S, Bagsvrd, Denmark) in 1 M $MgSO_4$. Cultures were incubated at 24° C. and 150 rpm until protoplasts formed. A volume of 35 ml of 2 M sorbitol was added to the protoplast digest and the mixture was centrifuged at 2500 rpm for 10 minutes. The pellet was resuspended, washed twice with STC, and centrifuged at 2000 rpm for 10 minutes to pellet the protoplasts. Protoplasts were counted with a hemocytometer and resuspended in an 8:2:0.1 solution of STC:SPTC:DMSO to a final concentration of $1.25\times10^7$ protoplasts/ml. The protoplasts were stored at −80° C., after controlled-rate freezing in a Nalgene Cryo 1° C. Freezing Container (VWR Scientific, Inc., San Francisco, Calif.).

Frozen protoplasts of *Fusarium venenatum* (Δtri5, Δdps1) were thawed on ice. A 100 μg quantity of pEJG66 were added to a 50 ml sterile polypropylene tube. Two ml of protoplasts were added to the tube, mixed gently, and incubated on ice for 30 minutes. Then 220 μl of SPTC was added and incubated 10 minutes at room temperature followed by 20 ml of SPTC and 10 minutes of further incubation at room temperature. The protoplasts were added to 500 ml of 40° C. VNO3RLMT top agarose and poured onto empty 150 mm diameter plates and incubated overnight at room temperature. Approximately 24 hours later, an additional 25 ml of 40° C. VNO3RLMT top agarose containing 10 mg of BASTA™ per ml was poured on top of each of the plates and incubated at room temperature for up to 14 days. The active ingredient in the herbicide BASTA™ is phosphinothricin. BASTA™ was obtained from AgrEvo (Hoechst Schering, Rodovre, Denmark) and was extracted twice with phenol:chloroform:isoamyl alcohol (25:24:1), and once with chloroform:isoamyl alcohol (24:1) before use.

Forty-two *Fusarium venenatum* transformants were obtained with pEJG66. The transformants were picked directly from the selection plates (VNO3RLMT underlay with VNO3RLMT-BASTA™ overlay) into 125 ml shake flasks containing 25 ml of M400 medium and incubated at 28° C., 200 rpm on a platform shaker for 7 days. The untransformed recipient strain was also included as a negative control.

Flasks were sampled at 4 and 7 days. Cells were removed by centrifugation. The cell-free culture broths from each transformant were assayed for chymotrypsin and trypsin activity using N-succinyl-Ala-Ala-Pro-Phe p-nitroanilide (chymotrypsin activity) and N-α-benzoyl-DL-arginine p-nitroanilide (trypsin activity), respectively, as the substrates using a microtiter plate assay. Specifically, N-succinyl-Ala-Ala-Pro-Phe p-nitroanilide (chymotrypsin activity) or N-α-benzoyl-DL-arginine p-nitroanilide (trypsin activity) was dissolved in DMSO at a concentration of 100 mg/ml and further diluted 1:50 in 100 mM MOPS buffer, 4 mM $CaCl_2$, 0.01% Triton X-100, pH 7.5 (assay buffer) to a 2 mg/ml solution. Ten μl of diluted enzyme broth (typically 1:10) was added to 90 μl of the assay buffer and 100 μl N-succinyl-Ala-Ala-Pro-Phe p-nitroanilide substrate for a final concentration of 1.6 mM (1.0 mg/ml). The rate of hydrolysis was measured kinetically at 405 nm and 30° C. for 3 minutes using a Molecular Devices 96-well plate reader (Sunnyvale, Calif.). *Fusarium venenatum* transformants #5, 7, 9, 10, 15, 24, 29, and 33 were found to produce significant chymotrypsin activity, but no trypsin activity.

The broth samples (15 μl) from *Fusarium venenatum* transformants #5, 7, 9, 10, 15, 24, 29, and 33 were also analyzed by SDS-PAGE using a Novex XCell II mini apparatus (Invitrogen, San Diego, Calif.). A 15 μl volume of each supernatant sample was heated to 95° C. for 5 minutes with an equal volume of Tris-glycine sample buffer (Invitrogen, San Diego, Calif.). The denatured supernatant proteins were separated on a 10-20% Tris-glycine gradient gel (Invitrogen, San Diego, Calif.) and stained with Coomassie blue. SDS-PAGE analysis showed that transformants #7, 9, 10 and 29 secrete a prominent polypeptide with an apparent molecular weight of approximately 22 kDa.

The highest chymotrypsin activity was obtained with *Fusarium venenatum* transformant #29. A 100 ml shake flask of the transformant was then grown for five days in M400 medium as above and harvested to provide protein for purification and characterization.

Example 4

Purification of *Fusarium oxysporum* Trypsin-Like Enzyme Engineered to a Polypeptide Having Chymotrypsin-Like Activity A 100 ml shake flask of *Fusarium venenatum* transformant #29 was cultivated for five days in M400 medium and harvested to provide protein for purification. The broth was filtered through MIRACLOTH™ and stored at −20° C. The thawed broth was clarified by centrifugation at 10,000×g for 20 minutes and the supernatant fraction was diluted with three volumes of deionized water. The protein solution was concentrated by ultrafiltration using a YM-3 membrane (Millipore, Bedford, Mass.). The concentrate was chromatographed on a 20 ml Q-Sepharose column pre-equilibrated in 20 mM MOPS pH 7 using a Pharmacia FPLC System (Amersham Biosciences, Piscataway, N.J.). Chymotrypsin activity was measured using N-succinyl-Ala-Ala-Pro-Phe p-nitroanilide as substrate according to the protocol described in Example 3. The chymotrypsin activity was found to flow directly through the column. The flow-through fractions were combined and concentrated by ultrafiltration using a YM-3 membrane. The concentrate was stored at −20° C. until further use.

The frozen sample (35 ml) was thawed, diluted to 100 ml with 50 mM sodium acetate pH 5, and the final pH was adjusted to 5 with 0.1 M HCl. The diluted sample was chromatographed on a 20 ml SP-Sepharose column pre-equilibrated in 50 mM sodium acetate pH 5. After washing the column with the equilibration buffer the chymotrypsin-like activity was eluted with a 0-0.3 M NaCl gradient in the same buffer. Fractions were assayed with benzoyl-arginine p-nitroanilide and N-succinyl-Ala-Ala-Pro-Phe p-nitroanilide, as described in Example 3. Protein with chymotrypsin activity eluted near the beginning of the gradient. Fractions were further analyzed by SDS-PAGE to determine the purity of the fractions. The SDS-PAGE analysis was performed using a Novex XCell II mini apparatus (Invitrogen, San Diego, Calif.) using a Tris-glycine 8-16% gel (Invitrogen, San Diego, Calif.). Active fractions with the greatest purity were pooled and concentrated using a PM-10 membrane (Amicon, Beverly, Mass.).

Example 5

Peptide Substrate Fingerprinting of the *Fusarium oxysporum* Trypsin-Like Enzyme Engineered to a Polypeptide Having Chymotrypsin-Like Activity N-Succinyl-Ala-Ala-Pro-X p-nitroanilide substrates, where X is Phe, Leu, Val, Met Ala, Glu, or Lys, were dissolved in DMSO (at a concentration of 100 mg/ml) and further diluted 1:50 in 100 mM MOPS buffer, 4 mM $CaCl_2$, 0.01% Triton X-100, pH 7.5 (assay buffer) for a 2 mg/ml solution. Ten μl of diluted enzyme broth (typically 1:10) was added to 90 μl assay buffer and 100 μl of N-succinyl-Ala-Ala-Pro-X-p-nitroanilide substrate for a final concentration of 1.6 mM (1.0 mg/ml). The rate of hydrolysis was measured kinetically at 405 nm and 30° C. for 3 minutes. The *Fusarium oxysporum* trypsin-like enzyme engineered to a polypeptide having chymotrypsin-like activity was compared to bovine chymotrypsin (Sigma Chemical Co., St. Louis, Mo.) and subtilisin A.

Figure 6:
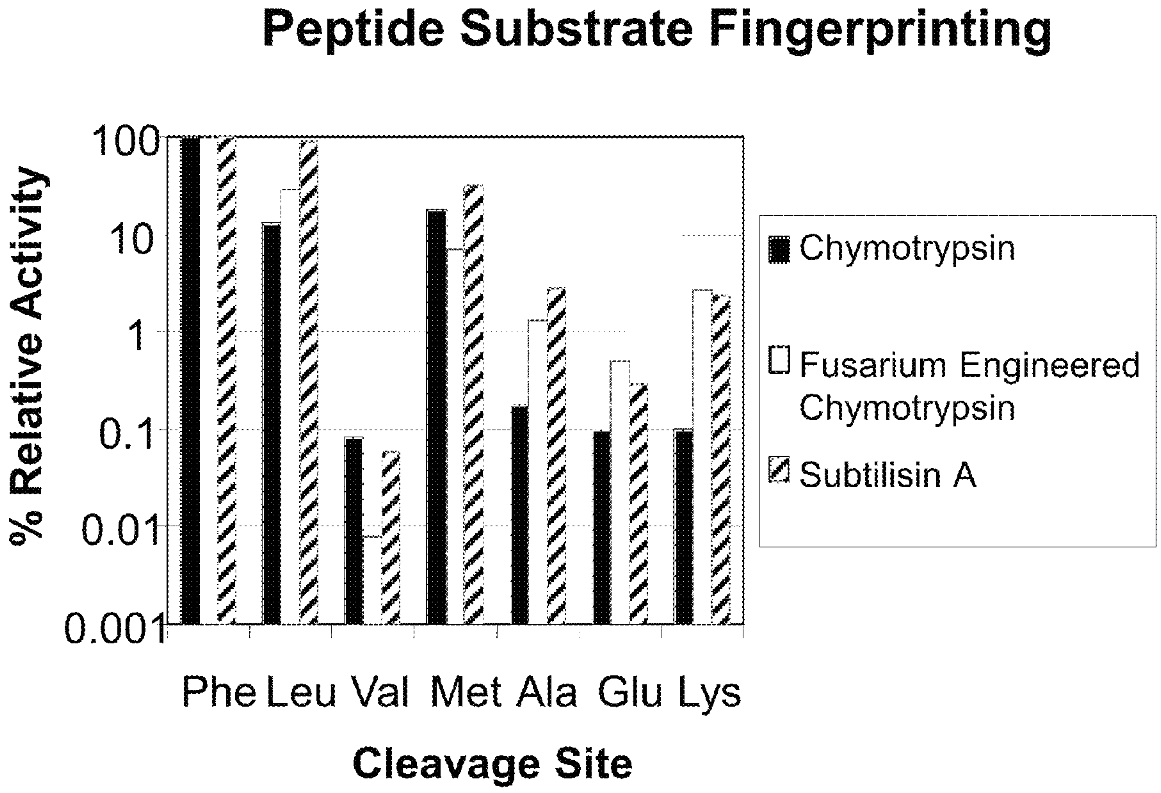
FIG. 6 shows peptide substrate fingerprinting of the *Fusarium oxysporum* trypsin-like enzyme engineered to encode a polypeptide having chymotrypsin-like activity relative to bovine chymotrypsin and subtilisin A.

Results were plotted as % Relative Activity to the preferred substrate N-succinyl-Ala-Ala-Pro-Phe-p-nitroanilide (FIG. 6). The results showed a similar substrate profile as bovine chymotrypsin.

Example 6

Protein Sequencing of the *Fusarium oxysporum* Trypsin-Like Enzyme Engineered to a Polypeptide Having Chymotrypsin-Like Activity N-Terminal amino acid sequencing of the purified *Fusarium* chymotrypsin-like enzyme was performed on an Applied Biosystems 476A Protein Sequencer (Applied Biosystems, Foster City, Calif.) with on-line HPLC and liquid phase trifluoroacetic acid (TFA) delivery. The purified chymotrypsin was spotted onto a TFA treated micro-filter with Biobrene™ and N-terminally sequenced utilizing liquid phase TFA delivery. Detection of phenylthiohydantoin-amino acids was accomplished by on-line HPLC using Buffer A containing 3.5% tetrahydrofuran in water with 18 ml of the Premix concentrate (Applied Biosystems, Foster City, Calif.) containing acetic acid, sodium acetate, and sodium hexanesulfonate and Buffer B containing acetonitrile. Data was collected and analyzed with a Macintosh IIsi using Applied Biosystems 610 Data Analysis software. Sequence determinations were made by visualizing chromatograms against a light source.

The purified chymotrypsin-like preparation was found to contain two sequences. The major protein was determined to have the predicted N-terminus: Ile-Val-Gly-Gly-Thr-Ser-Ala-Ser-Ala-Gly-Asp-Phe-Pro-Phe-Ile (amino acids 25 to 39 of SEQ ID NO: 4) with the pro-peptide removed. The minor protein contained an internal fragment at Gly179: Gly-Thr-Ser-Ala-Ile-Thr-Asn-Gln-Met-Phe (amino acids 179 to 188 of SEQ ID NO: 4). This internal fragment followed a tyrosine and was most likely due to chymotrypsin-like autoproteolysis.

Example 7

Characterization of the *Fusarium oxysporum* Trypsin-Like Enzyme Engineered to a Polypeptide Having Chymotrypsin-Like Activity The purified chymotrypsin-like enzyme described in Example 4 was characterized with regard to its temperature stability, pH optimum, and theoretical coefficient.

Figure 7:
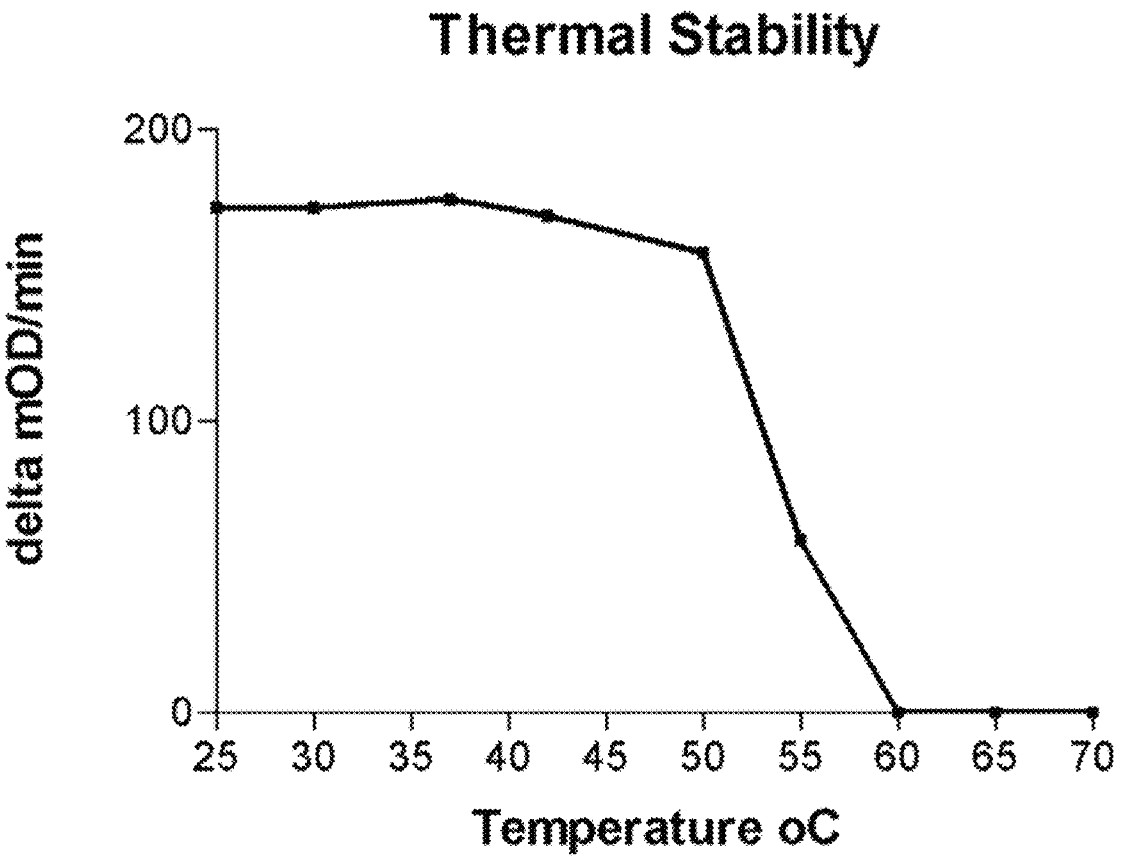
FIG. 7 shows the temperature stability of the *Fusarium oxysporum* trypsin-like enzyme engineered to encode a polypeptide having chymotrypsin-like activity.
Figure 8:
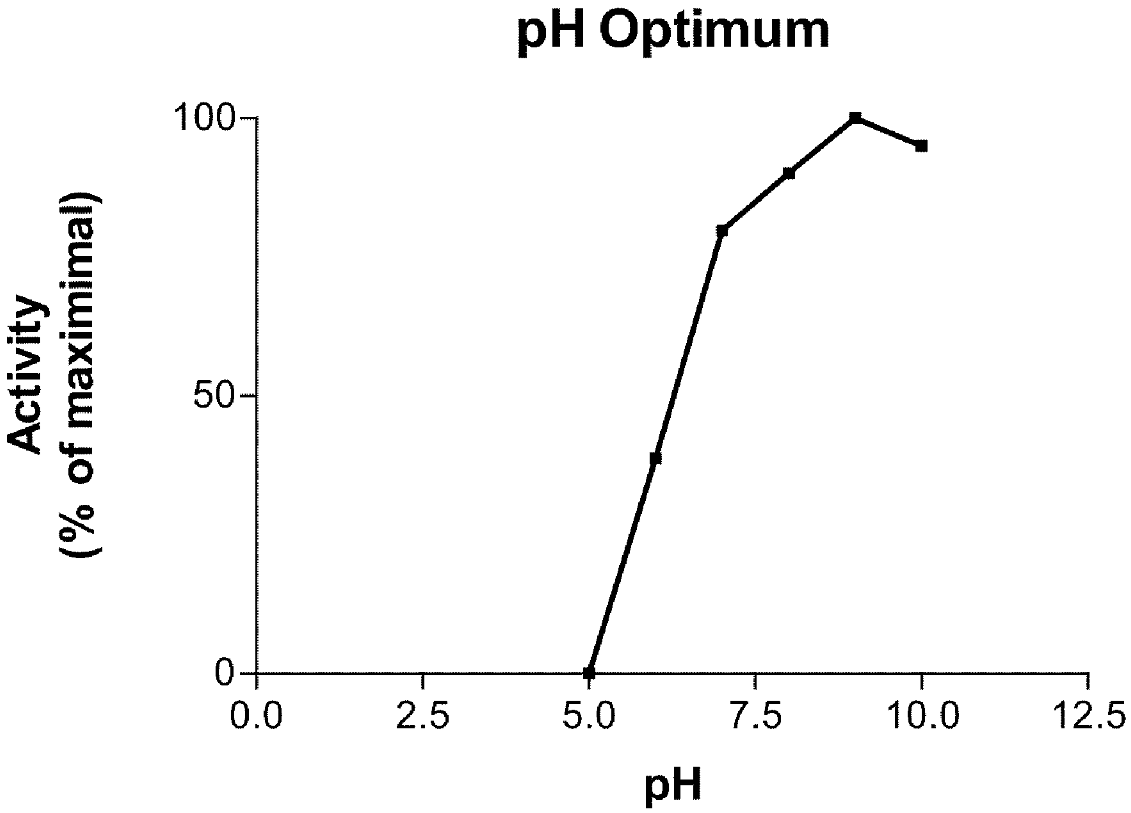
FIG. 8 shows the pH optimum of the *Fusarium oxysporum* trypsin-like enzyme engineered to encode a polypeptide having chymotrypsin-like activity.

Temperature Stability. Fifty μl of the purified enzyme in 100 mM MOPS, 4 mM $CaCl_2$, 0.01% Triton X-100 buffer, pH 7.5, was incubated at various temperatures (25, 30, 37, 42, 50, 55, 60, 65, and 70° C.) for 60 minutes. The reactions were stopped by placing on ice. Samples of 20 μl at each temperature were assayed for residual activity using N-succinyl-Ala-Ala-Pro-Phe as a substrate as described in Example 3. The results showed that the chymotrypsin-like activity dropped off significantly above 50° C. (FIG. 7).

pH Optimum. N-Succinyl-Ala-Ala-Pro-Phe-p-nitroanilide (100 mg/ml in DMSO) was diluted 1:50 into B&R Universal Buffer at various pH values. Twenty μl of pre-diluted (1:10) purified enzyme solution was mixed with 80 μl of Universal Buffer and 100 μl substrate, giving a final substrate concentration of 1.6 mM. The reaction was incubated 3 minutes at 30° C. and monitored by reading kinetically at 405 nm. Ten μl of 2 N NaOH was added to stop the reaction and raise the pH for color development, and the absorbance was measured at 405 nm. The pH optimum was determined to be 9.0 (FIG. 8).

Theoretical Extinction Coefficient. The protein sequence was used to determine a theoretical extinction coefficient of the enzyme at λ=280 nm according to the method of C. Nick Pace, et al., 1995, *Protein Science* 4 2411-2433. The theoretical extinction coefficient of the chymotrypsin-like enzyme was determined to be 1.20 $M^{-1}cm^{-1}$.

Deposit of Biological Material

The following biological material has been deposited under the terms of the Budapest Treaty with the Agricultural Research Service Patent Culture Collection, Northern Regional Research Center, 1815 University Street, Peoria, Ill., 61604, and given the following accession number:

| Deposit | Accession Number | Date of Deposit |
|---|---|---|
| *E. coli* pEJG66.1XLGOLD | NRRL B-30627 | Sep. 6, 2002 |

The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. A method for obtaining a variant of a microbial trypsin, comprising:

(a) introducing the specific combination of modifications as follows:

substitutions at positions corresponding to positions 144, 193, 198, 201, 218, 223, 227, 228, 229, 230, and 231 of amino acids 25 to 248 of SEQ ID NO: 2;

deletions at positions corresponding to positions 192, 197, and 226 of amino acids 25 to 248 of SEQ ID NO: 2; and an insertion between positions corresponding to positions 224 and 225 of amino acids 25 to 248 of SEQ ID NO: 2;

wherein, the variant has chymotrypsin activity and (i) has at least 90% identity to amino acids 25 to 248 of SEQ ID NO: 2; or (ii) is encoded by a nucleotide sequence which hybridizes under at least medium-high stringency conditions with nucleotides 202 to 801 of SEQ ID NO: 1 or the complete complementary strand thereto, wherein medium-high stringency conditions are defined as prehybridization and hybridization at 42° C. in 5×SSPE, 0.3% SDS, 200 μg/ml sheared and denatured salmon sperm DNA, and 35% formamide followed by washing three times each for 15 minutes using 2×SSC, 0.2% SDS at 60° C.; and (b) expressing the variant in a host cell, and (c) recovering the variant.

2. The method of claim 1, wherein the variant is encoded by the nucleotide sequence contained in pEJG66.1XLGOLD, which is contained in *E. coli* NRRL B-30627.

3. The method of claim 1, wherein the variant is in a form of a precursor comprising amino acids 1 to 24 of SEQ ID NO: 2 as a prepro region, or a portion thereof, linked in translation reading frame with the amino terminus of the variant.

4. The method of claim 1, which comprises the substitutions V144T+S193A+D198S+Q201M+A218I+N223S+R227S+P228T+N229S+Y230T+5231 P, the deletions V192*+K197*+A226*, and the insertion G224GT of amino acids 25 to 248 of SEQ ID NO: 2.

5. The method of claim 1, wherein the trypsin polypeptide has an amino acid sequence which has at least 90% identity to amino acids 25 to 248 of SEQ ID NO. 2.

6. The method of claim 5, wherein the trypsin polypeptide has an amino acid sequence which has at least 95% identity to amino acids 25 to 248 of SEQ ID NO: 2.

7. The method of claim 6, wherein the trypsin polypeptide has an amino acid sequence which has at least 97% identity to amino acids 25 to 248 of SEQ ID NO: 2.

8. The method of claim 1, wherein the trypsin polypeptide has the amino acid sequence of amino acids 25 to 248 of SEQ ID NO: 2.

9. The method of claim 1, wherein the trypsin polypeptide is encoded by a nucleotide sequence which hybridizes under medium-high stringency conditions with nucleotides 202 to 801 of SEQ ID NO: 1 or the complete complementary strand thereto, wherein medium-high stringency conditions are defined as prehybridization and hybridization at 42° C. in 5×SSPE, 0.3% SDS, 200 μg/ml sheared and denatured salmon sperm DNA, and 35% formamide followed by washing three times each for 15 minutes using 2×SSC, 0.2% SDS at 60° C.

10. The method of claim 9, wherein the trypsin polypeptide is encoded by a nucleotide sequence which hybridizes under high stringency conditions with nucleotides 202 to 801 of SEQ ID NO: 1 or the complete complementary strand thereto, wherein high stringency conditions are defined as prehybridization and hybridization at 42° C. in 5×SSPE, 0.3% SDS, 200 μg/ml sheared and denatured salmon sperm DNA, and 50% formamide followed by washing three times each for 15 minutes using 2×SSC, 0.2% SDS at 65° C.

11. The method of claim 10, wherein the trypsin polypeptide is encoded by a nucleotide sequence which hybridizes under very high stringency conditions with nucleotides 202 to 801 of SEQ ID NO: 1 or the complete complementary strand thereto, wherein very high stringency conditions are defined as prehybridization and hybridization at 42° C. in 5×SSPE, 0.3% SDS, 200 μg/ml sheared and denatured salmon sperm DNA, and 50% formamide followed by washing three times each for 15 minutes using 2×SSC, 0.2% SDS at 70° C.

12. The method of claim 1, wherein the trypsin polypeptide is a wild-type trypsin polypeptide.

13. The method of claim 1, wherein the variant comprises amino acids 25 to 246 of SEQ ID NO: 4.

14. The method of claim 1, wherein the variant has at least 90% identity to amino acids 25 to 248 of SEQ ID NO: 2.

* * * * *